US012767666B2

(12) United States Patent
Tanaka et al.

(10) Patent No.: US 12,767,666 B2
(45) Date of Patent: Oct. 20, 2026

(54) COMPLEX, AND USE THEREOF

(71) Applicant: RIKEN, Saitama (JP)

(72) Inventors: Katsunori Tanaka, Saitama (JP); Ambara Rachmat Pradipta, Saitama (JP)

(73) Assignee: RIKEN, Saitama (JP)

( * ) Notice: Subject to any disclaimer, the term of this patent is extended or adjusted under 35 U.S.C. 154(b) by 677 days.

(21) Appl. No.: 18/029,947

(22) PCT Filed: Oct. 13, 2021

(86) PCT No.: PCT/JP2021/037805
§ 371 (c)(1),
(2) Date: May 22, 2023

(87) PCT Pub. No.: WO2022/085523
PCT Pub. Date: Apr. 28, 2022

(65) Prior Publication Data
US 2024/0002398 A1 Jan. 4, 2024

(30) Foreign Application Priority Data
Oct. 23, 2020 (JP) ................................ 2020-178209

(51) Int. Cl.
*C07D 498/08* (2006.01)

(52) U.S. Cl.
CPC ................................ *C07D 498/08* (2013.01)

(58) Field of Classification Search
None
See application file for complete search history.

(56) References Cited

U.S. PATENT DOCUMENTS

2021/0179853 A1 6/2021 Tanaka et al.

FOREIGN PATENT DOCUMENTS

WO 2020/009227 1/2020

OTHER PUBLICATIONS

Yoshida et al., Scientific Reports, 1(82), 1-4 (Year: 2011).*
Calder et al., Hypoxia-activated pro-drugs of the KDAC inhibitor vorinostat (SAHA), Tetrahedron, 2020, vol. 78, Issue 21, Article 131170, 8 pages.

(Continued)

*Primary Examiner* — George W Kosturko
*Assistant Examiner* — Jason M. Nolan
(74) *Attorney, Agent, or Firm* — Casimir Jones, S.C.; Robert A. Goetz

(57) ABSTRACT

A complex in accordance with an embodiment of the present invention contains: an acrolein-reactive site having a chemical structure represented by Formula (1); and a leaving site having another chemical structure. The leaving site is binding to the acrolein-reactive site via a linker that is cleavable by a reaction between the acrolein-reactive site and acrolein.

(1)

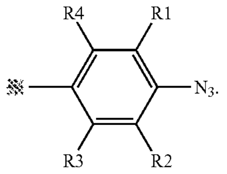

9 Claims, 14 Drawing Sheets

(56) References Cited

OTHER PUBLICATIONS

Herrlinger et al., Nitroreductase-Mediated Release of Inhibitors of Lysine-Specific Demethylase 1 . . . , ChemBioChem, 2020, 21(16), p. 2329-2347.
Brakel et al., A Doxorubicin Prodrug Activated by the Staudinger Reaction, Bioconjugate Chem., 2008, 19, 714-718.
Pradipta, A. et al. Uncatalyzed Click Reaction between Phenyl Azides and Acrolein . . . , ACS Sens. 2016, 1, 623-632.
Matikonda, S. Siddharth et al., "Bioorthogonal prodrug activation driven by . . . ", Chemical Science, 2015, vol. 6, pp. 1212-1218.
Matikonda, S. Siddharth et al., "Mechanistic Evaluation of Bioorthogonal Decaging with . . . ", Bioconjugate Chemistry, Jan. 12, 2018, vol. 29, pp. 324-334.
Pradipta, R. Ambara et al. Targeted 1,3-dipolar cycloaddition wilh acrolein for cancer prodrug activation, Chemical Science, Apr. 1, 2021, vol. 12, pp. 5438-5449.
Written Opinion for PCT/JP2021/037805 and its English Translation, dated Dec. 14, 2021, 8 pages.
International Search Report for PCT/JP2021/037805 and its English Translation, dated Dec. 14, 2021, 4 pages.
European Search Report For EP Patent Application No. 21882664.2, dated Sep. 12, 2025, 11 pages.
Ambara R. Pradipta et al: "Uncatalyzed Click Reaction between Phenyl Azides and Acrolein: 4-Formyl-1,2,3-Triazolines as "Clicked" Markers for Visualizations of Extracellular Acrolein Released from Oxidatively Stressed Cells", ACS Sensors, vol. 1, No. 5, Apr. 12, 2016 (Apr. 12, 2016), pp. 623-632, XP055673662.
Remco Van Brakel et al: "A Doxorubicin Prodrug Activated by the Staudinger Reaction", Bioconjugate Chemistry, vol. 19, No. 3, Mar. 1, 2008 (Mar. 1, 2008), pp. 714-718, XP055040656.
Office Action for JP Patent Application No. 2022-557022, dated Feb. 3, 2026, 5 pages.

* cited by examiner

Prodrug PUR-ABC S6

COMPLEX, AND USE THEREOF

TECHNICAL FIELD

The present invention relates to a complex and use thereof.

BACKGROUND ART

In cancer targeting therapy, development of a drug delivery system aimed at optimizing treatment by enhancing drug efficacy while inhibiting side effects is underway. The drug delivery system makes it possible to selectively deliver a drug to a specific tissue (target tissue) that needs to be treated, and to reduce side effects by lowering influence on a normal tissue.

For example, study has been carried out on a prodrug that exhibits antitumor activity under conditions characteristic to tumor cells such as a hypoxic environment in order to deliver a drug to a target tumor cell (Non-patent Literatures 1 and 2). Furthermore, study has been carried out on a prodrug that releases a drug by reacting with a specific compound that serves as a trigger (Non-patent Literatures 3 and 4).

However, the compounds disclosed in Non-patent Literatures 1 through 4 are still in the test-tube stage, and in addition, the compounds disclosed in Non-patent Literatures 3 and 4 each require an additional compound as a trigger for drug release.

Acrolein ($CH_2$=CHCHO) is the smallest-sized unsaturated aldehyde molecule and is a very highly reactive molecule. Acrolein is known to be generated during burning of an organic matter. In addition, for example, in oxidative stress-related diseases such as cancer, Alzheimer's disease, and cerebral infarction, acrolein is considered to be generated in vivo in the form of a lipid metabolite or a polyamine metabolite.

Furthermore, a recent study has made it clear that acrolein is more toxic than a hydroxy radical, which has been considered as the main cause of oxidative stress. Thus, attention has been paid in recent years particularly to (i) detection of acrolein that is generated in a cell and (ii) elucidation of a relationship between an oxidative stress-related disease and acrolein. For example, Non-patent Literature 5 discloses a novel compound that selectively reacts particularly with acrolein among molecules that are present in a living organism.

CITATION LIST

Non-Patent Literature

[Non-Patent Literature 1]
Calder et. al., Tetrahedron, 2020, Volume 78, Issue 21, Article 131170
[Non-Patent Literature 2]
Herrlinger et. al., ChemBioChem, 2020, 21(16), p 2329-2347
[Non-Patent Literature 3]
Brakel et. al., Bioconjugate Chem., 2008, 19, 714-718
[Non-Patent Literature 4]
Matikonda et al., Chem. Sci., 2015, 6, 1212-1218
[Non-Patent Literature 5]
ACS Sens. 2016, 1, 623-632.

SUMMARY OF INVENTION

Technical Problem

However, use of a compound that reacts with acrolein in a prodrug or the like has not been substantially studied previously.

Under the circumstances, an object of the present invention is to provide, for example, (i) a novel complex that reacts with acrolein to release an active substance and (ii) use thereof.

Solution to Problem

In order to attain the object, the present invention includes aspects described below.

A complex containing: an acrolein-reactive site having a chemical structure represented by Formula (1); and a leaving site having another chemical structure, the leaving site binding to the acrolein-reactive site via a linker that is cleavable by a reaction between the acrolein-reactive site and acrolein, (1)

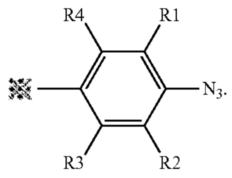

wherein

R1 and R2 each independently represent a hydrogen atom, a halogen atom, or an alkyl group that has 1 to 5 carbon atoms and that may be substituted by at least one halogen atom, provided that at least one of R1 and R2 is the alkyl group having 1 to 5 carbon atoms;

R3 and R4 each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms (provided that a hydrogen atom constituting the alkyl group may be substituted by a substituent selected from a halogen atom, a hydroxy group, and an amino group that may have a substituent); and ※ is a binding site to the linker.

Advantageous Effects of Invention

According to an aspect of the present invention, it is possible to provide, for example, (i) a novel complex that reacts with acrolein to release an active substance and (ii) use thereof.

DESCRIPTION OF EMBODIMENTS

1. Complex

Figure 1:
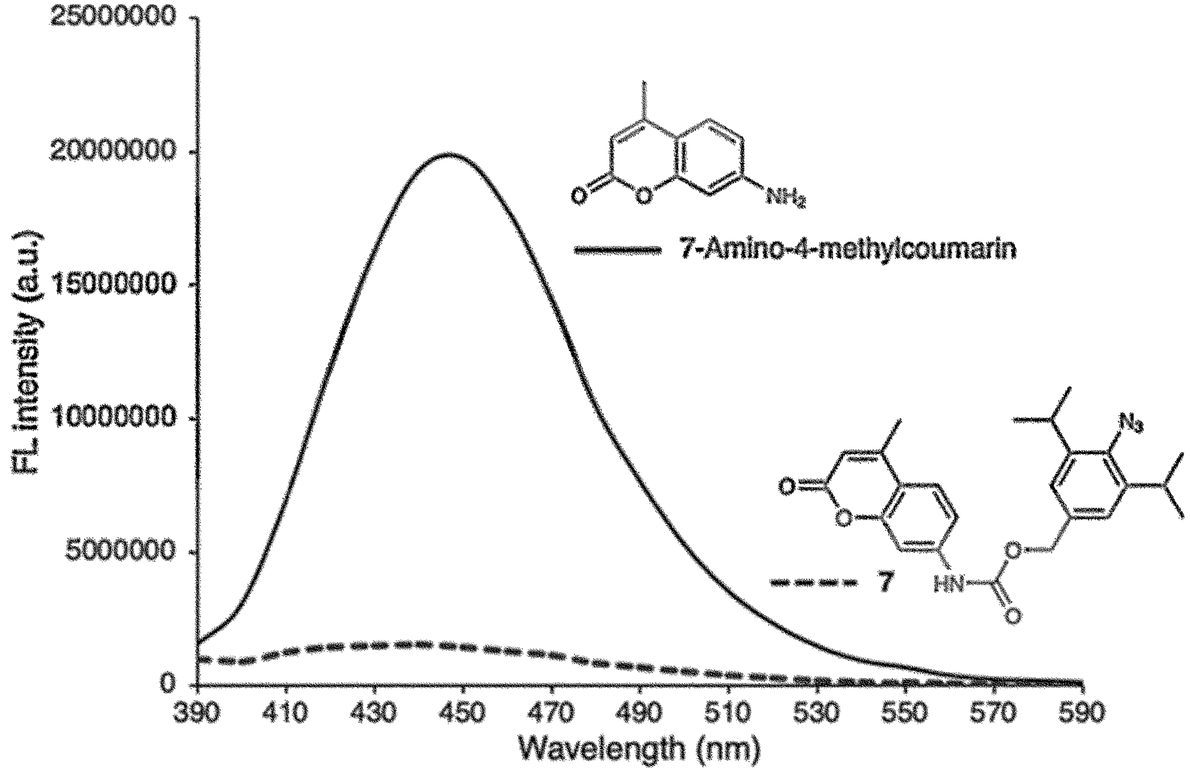
FIG. 1 is a diagram indicating fluorescence spectra obtained by fluorescence measurement of a complex in accordance with an aspect of the present invention (coumarin-ABC) and a control (coumarin).

A complex in accordance with an embodiment of the present invention (hereinafter simply referred to also as "present complex") contains: an acrolein-reactive site having a chemical structure represented by Formula (1); and a leaving site having another chemical structure, the leaving site binding to the acrolein-reactive site via a linker that is cleavable by a reaction between the acrolein-reactive site and acrolein.

(1)

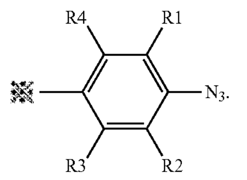

The present complex reacts sharply with acrolein in the presence of acrolein (2-propenal, $CH_2{=}CHCHO$) to cleave the linker and release the leaving site. This is because an azide group ($N_3$ group) in the acrolein-reactive site of the present complex, as a 1.3-dipole, causes a 1.3-dipole cycloaddition reaction (click reaction) with acrolein which is a dipolarophile agent to produce a 5-membered ring (1,2,3-triazoline) which is an intermediate.

The 1,2,3-triazoline produced by the click reaction (1.3-dipole cycloaddition reaction) between the acrolein-reactive site and acrolein then forms imine through an isomerization reaction. Subsequently, the linker between the acrolein-reactive site and the leaving site is cleaved in association with decarboxylation (leaving of carbon dioxide). This separates a diazo compound derived from the acrolein-reactive site from an active substance derived from the leaving site.

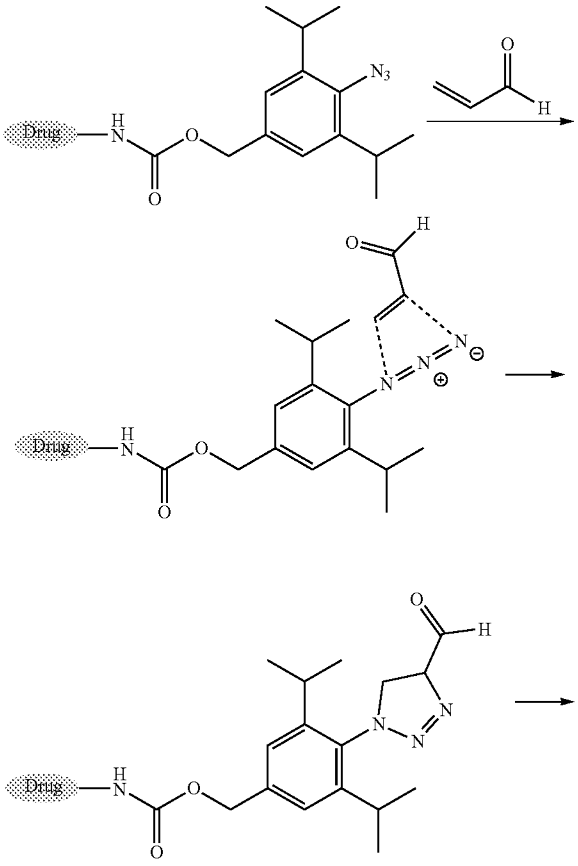

-continued

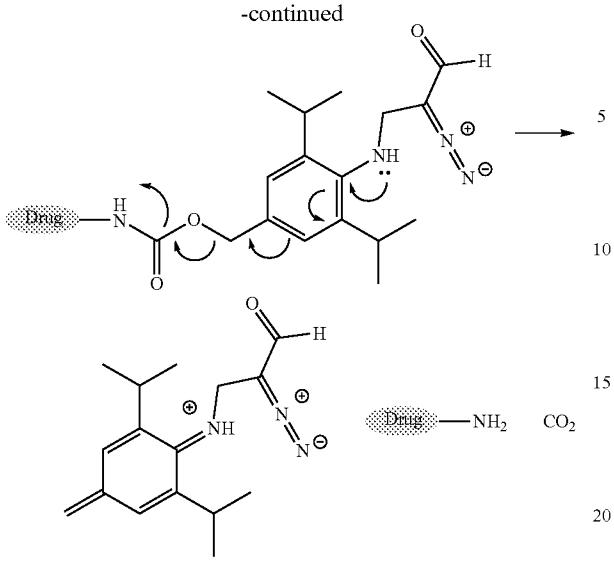

The above reaction is capable of progressing under a mild condition in a living organism or the like, and exhibits high reaction specificity. Therefore, by administering the present complex into a living organism, endogenous acrolein reacts with the present complex, and consequently an active substance derived from the leaving site can be released into the living organism.

R1 and R2

In Formula (1), R1 and R2 each independently represent a hydrogen atom, a halogen atom, or an alkyl group that has 1 to 5 carbon atoms and that may be substituted by at least one halogen atom. Note, however, that at least one of R1 and R2 is the alkyl group having 1 to 5 carbon atoms.

Examples of the halogen atom include a fluorine atom, a chlorine atom, a bromine atom, and the like. Note that the fluorine atom may be an isotope.

The alkyl group having 1 to 5 carbon atoms may be either linear or branched. The alkyl group has a hydrogen atom that may be substituted or unsubstituted by the at least one halogen atom. Examples of the alkyl group that has 1 to 5 carbon atoms and that has an unsubstituted hydrogen atom include a methyl group, an ethyl group, a propyl group, an isopropyl group, an n-butyl group, an isobutyl group, a tert-butyl group, an n-pentyl group, an isopentyl group, a tert-pentyl group, and a sec-pentyl group.

R1 and R2 may be identical to or different from each other. In order to achieve a higher reactivity with acrolein, R1 and R2 may each be preferably an alkyl group that has 1 to 5 carbon atoms and that is substituted or unsubstituted by the at least one halogen atom, and may be more preferably alkyl groups that are identical to each other. Note that preferably 1 to 4 carbon atoms, and more preferably 2, 3, or 4 carbon atoms may constitute the alkyl group.

In another aspect, it may be preferable that one of R1 and R2 be the alkyl group that has 1 to 5 carbon atoms and that is substituted or unsubstituted by the at least one halogen atom and that the other one of R1 and R2 be the halogen atom (in particular, a fluorine or isotope). Note that preferably 1 to 4 carbon atoms, and more preferably 2, 3, or 4 carbon atoms may constitute the alkyl group.

R3 and R4

In Formula (1), R3 and R4 each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms. Note, however, that a hydrogen atom constituting the alkyl group may be substituted by a substituent selected from a halogen atom, a hydroxy group, and an amino group that may have a substituent.

The definition and exemplary description of the halogen atom are similar to that described in R1 and R2.

Examples of the amino group that may have a substituent include an unsubstituted amino group, an alkylamino group, a (hetero)aryl amino group, and the like. For example, 1 to 5 carbon atoms constitute each alkyl group included in the alkylamino group. The (hetero)aryl amino group refers to a group in which at least one hydrogen atom constituting the amino group is substituted by an aryl group (i.e., an aryl group or a heteroaryl group) that may have a hetero atom. Examples of each (hetero)aryl group included in the (hetero) aryl amino group include, for example, a (hetero)aryl group in which 3 to 20 (preferably 4 to 12) atoms form a framework of a ring structure. Note that examples of the hetero atom included in the heteroaryl group include a sulfur atom, a nitrogen atom, and an oxygen atom.

Examples of the alkoxy group having 1 to 5 carbon atoms include a methoxy group, an ethoxy group, a propoxy group, an isopropoxy group, and a butoxy group.

Examples of the alkylthio group having 1 to 5 carbon atoms include a methylthio group, an ethylthio group, a propylthio group, a butylthio group, and a pentylthio group.

The definition and exemplary description of the alkyl group that has 1 to 5 carbon atoms and that has an unsubstituted hydrogen atom are similar to that described in R1 and R2. Note that preferably 1 to 4 carbon atoms, and more preferably 1 to 3 carbon atoms may constitute the alkyl group. Note, however, that at least one of hydrogen atoms constituting the alkyl group may be substituted by a substituent selected from a halogen atom, a hydroxy group, and an amino group that may have a substituent. Note here that examples of the halogen atom and of the amino group that may have a substituent include examples identical to those mentioned as R3 and R4.

R3 and R4 may be identical to or different from each other. Note, however, that R3 and R4 may be preferably identical to each other.

R3 and R4 may be preferably each independently a hydrogen atom, a halogen atom, or an alkyl group that has 1 to 5 carbon atoms and that may be substituted by at least one halogen atom. The definition and exemplary description of the alkyl group that has 1 to 5 carbon atoms and that may be substituted by at least one halogen atom are similar to that described in R1 and R2.

Exemplary Description of Preferable Combination of R1, R2, R3, and R4 Located on Single Ring Exemplary description of combination <1>: In Formula (1), R1, R2, R3, and R4 each independently represent a hydrogen atom, a halogen atom, or an alkyl group that has 1 to 5 carbon atoms and that may be substituted by at least one halogen atom, provided that at least one of R1 and R2 is the alkyl group having 1 to 5 carbon atoms.

Exemplary description of combination <2>: In Formula (1), R3, and R4 each independently represent a hydrogen atom, a halogen atom, or an alkyl group that has 1 to 5 carbon atoms and that may be substituted by at least one halogen atom, and R1 and R2 are each the alkyl group having 1 to 5 carbon atoms.

Exemplary description of combination <3>: In Formula (1), R3 and R4 each independently represent a hydrogen atom, a halogen atom, or an alkyl group that has 1 to 5 carbon atoms and that may be substituted by at least one halogen atom, and one of R1 and R2 is the alkyl group having 1 to 5 carbon atoms, and the other one of R1 and R2 is a halogen atom.

Exemplary description of combination <4>: In Exemplary description of combination <1> or <2> above, R3 and R4 are each independently the hydrogen atom or the halogen atom, and R1 and R2 are each the alkyl group having 1 to 5 carbon atoms.

Exemplary description of combination <5>: In Exemplary description of combination <3> above, R3 and R4 are each independently the hydrogen atom or the halogen atom.

※

In Formula (1), ※ is a binding site to the linker for connecting the leaving site as described above. The linker is cleavable by a reaction between the acrolein-reactive site and acrolein. More specifically, the linker has a structure in which a cleavage is facilitated by a 5-membered ring that is produced by a 1.3-dipole cycloaddition reaction between the acrolein-reactive site and acrolein.

Linker

Examples of the linker that is cleavable by a reaction between the acrolein-reactive site and acrolein include a linker having a chemical structure represented by Formula (2).

(2)

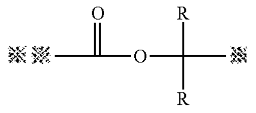

R

In Formula (2), two R each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms. Note, however, that a hydrogen atom constituting the alkyl group may be substituted by a substituent selected from a halogen atom, a hydroxy group, and an amino group that may have a substituent.

The definition and exemplary description of the halogen atom are similar to that described in R1 and R2.

The definition and exemplary description of the amino group that may have a substituent are similar to that described in R3 and R4.

Examples of the alkoxy group having 1 to 5 carbon atoms include a methoxy group, an ethoxy group, a propoxy group, an isopropoxy group, and a butoxy group.

Examples of the alkylthio group having 1 to 5 carbon atoms include a methylthio group, an ethylthio group, a propylthio group, a butylthio group, and a pentylthio group.

The definition and exemplary description of the alkyl group that has 1 to 5 carbon atoms and that has an unsubstituted hydrogen atom are similar to that described in R1 and R2. Note that preferably 1 to 4 carbon atoms, and more preferably 1 to 3 carbon atoms may constitute the alkyl group. Note, however, that at least one of hydrogen atoms constituting the alkyl group may be substituted by a substituent selected from a halogen atom, a hydroxy group, and an amino group that may have a substituent. Note here that examples of the halogen atom and of the amino group that may have a substituent include examples identical to those mentioned as R3 and R4.

Two R that bind to a single carbon atom may be identical to or different from each other. Note, however, that two R may be preferably identical to each other.

Two R may be preferably each independently a hydrogen atom, a halogen atom, or an alkyl group having 1 to 5 carbon atoms (provided that a hydrogen atom constituting the alkyl group may be substituted by a substituent selected from a halogen atom, a hydroxy group, and an amino group that may have a substituent). Alternatively, two R may be preferably each independently a hydrogen atom, a halogen atom, or an alkyl group that has 1 to 5 carbon atoms and that may be substituted by at least one halogen atom. The definition and exemplary description of the alkyl group that has 1 to 5 carbon atoms and that may be substituted by at least one halogen atom are similar to that described in R1 and R2.

※ and ※※

In Formula (2), ※※ is a binding site to the leaving site. From the viewpoint of rapid cleavage of the linker, E may be preferably a binding site to a nitrogen atom, a sulfur atom, or an oxygen atom contained in the leaving site (i.e., —N(−)—, —S—, or —O—), or may be more preferably a binding site to a nitrogen atom contained in the leaving site.

In Formula (2), E is a binding site to the acrolein-reactive site. Therefore, the present complex containing the linker having the chemical structure represented by Formula (2) has a chemical structure represented by Formula (3) below.

(3)

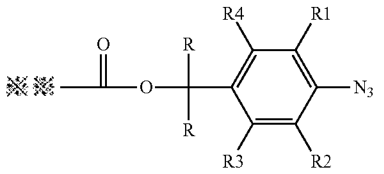

In Formula (3), the definition and exemplary description of R1, R2, R3, R4, and R are similar to that described in the descriptions of Formula (1) and Formula (2). Furthermore, in Formula (3), ※※ is similar to that described in the description of Formula (2).

Specific examples of the present complex having the chemical structure represented by Formula (3) include a complex (leaving site-ABC) of a leaving site and 4-azide benzyl carbamate (hereinafter simply referred to also as "ABC") represented by Formula (4) below.

(4)

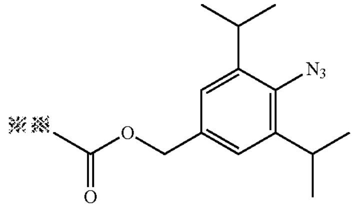

In Formula (4), ※※ is a binding site to a nitrogen atom contained in the leaving site. Note that, in a case where E is a binding site to a nitrogen atom contained in the leaving site, the chemical structures represented by Formulae (3) and (4) can also be each regarded as a protecting group for the amino group contained in the leaving site, where deprotection can be made by acrolein.

Reaction Mechanism of Linker Cleavage

The following description will discuss a reaction mechanism in which a linker having the chemical structure represented by Formula (2) is cleaved and a leaving site (active substance) is released, with reference to an example in which a linker binds to a nitrogen atom included in the leaving site in the complex in accordance with an aspect of the present invention.

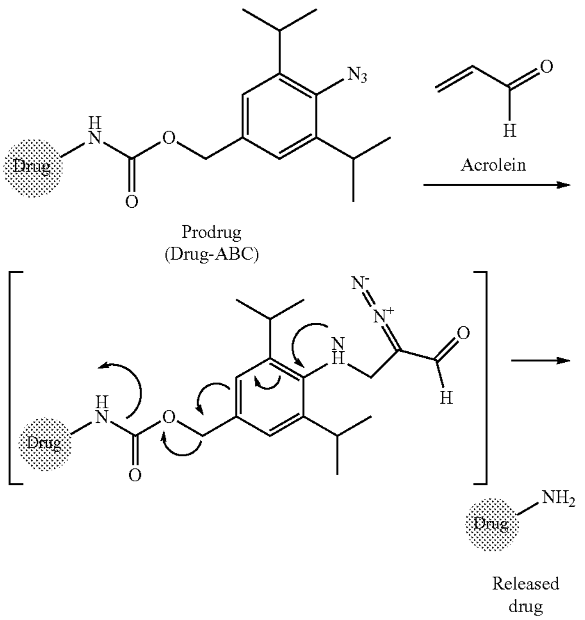

When the present complex approaches acrolein, an azide group of the present complex and the acrolein generate 1,2,3-triazoline as an intermediate by a 1.3-dipole cycloaddition reaction. In the 1,2,3-triazoline, its five-membered ring (triazole ring) opens to generate a diazo compound, and intramolecular electron transfer is initiated. This results in a cleavage between carbonyl carbon contained in the linker and the nitrogen atom contained in the leaving site, and the leaving site is released as an active substance.

Leaving Site

As the leaving site, any compound that is intended to be released in a region where acrolein is present can be used. Examples of such a compound include antitumor compounds and labelled compounds such as a coloring reagent and a marker.

The leaving site is preferably a compound having a nitrogen atom, a sulfur atom, or an oxygen atom as a binding site to the linker so that the leaving site can be rapidly cleaved from the linker. Furthermore, in order to facilitate binding to the linker, the leaving site may preferably have a hydroxyl group, a carboxy group, a thiol group, or an amino group.

Preferably, binding of the leaving site to the linker is in a mode that can be rapidly cleaved by a reaction between the acrolein-reactive site and acrolein. From this viewpoint, it is preferable that the binding between the leaving site and the linker is a carbamate bond, a thiocarbamate bond, an ester bond, or a thioester bond.

Antitumor Compound

It has been found by the inventors of the present invention that acrolein is more generated in a tumor cell than in a normal cell, and the amount thereof is up to not less than 1,000 times greater than that in an inflammation site in a normal cell (Tanaka, K. et al. Adv. Sci. 2019, 6, 1801479; Tanaka, K. et al. Bioorg. Med. Chem. 2019, 27, 2228; Tanaka, K. et al. Adv. Sci. 2020, 1901519). The present complex containing the antitumor compound as the leaving site can react with acrolein that is present around a tumor cell to release the antitumor compound. Therefore, the present complex can be suitably used as a therapeutic agent for tumors.

As an antitumor compound used as the leaving site, all compounds including antitumor compounds that are used in clinical practice or clinical test and antitumor compounds that will be developed in the future can be used without limitation, provided that the compounds each have activity of killing a tumor cell in a living organism, like an anticancer drug, a low-molecular target agent, a radionuclide, and the like.

A molecular weight of the antitumor compound is not particularly limited, and is preferably a low molecular weight enough to reach a tumor cell. For example, the molecular weight of the antitumor compound is not more than 15,000 Da, preferably not more than 10,000 Da, and more preferably not more than 500 Da. A lower limit of the molecular weight of the antitumor compound is not particularly limited. For example, the molecular weight of the antitumor compound is not less than 100 Da, and preferably not less than 300 Da.

The antitumor compound is preferably in a state in which its antitumor activity (toxicity) is weakened while being bound to the acrolein-reactive site via a linker, as compared to a state of not binding. That is, the antitumor compound is preferably in the form of a prodrug.

Examples of the antitumor compound suitably used as the leaving site include, but not limited to, mitomycin C, doxorubicin, dacarbazine, crizotinib, endoxifen, and a camptothecin derivative [e.g., an active body part of DS-8201 (trastuzumab deruxtecan) (code name: DXd, chemical name: N[(1-S,9S)-9-ethyl-5-fluoro-2,3,9,10,13,15-hexahydro-9-hydroxy-4-methyl-10,13-dioxo-1H,12H-benzo[de]pyrano[3',4':6,7]indolizino[1,2-b]quinolin-1-yl]-2-hydroxyacetamide, see Drug Delivery System Vol. 34, No. 1 (2019) p. 52-58, "Development of novel DNA topoisomerase I inhibitor based ADC technology" by Yuki Abe, Takashi Nakada, and Toshinori Agatsuma)].

Specific examples of the present complex having mitomycin C as the leaving site include mitomycin C-ABC represented by the following chemical structural formula.

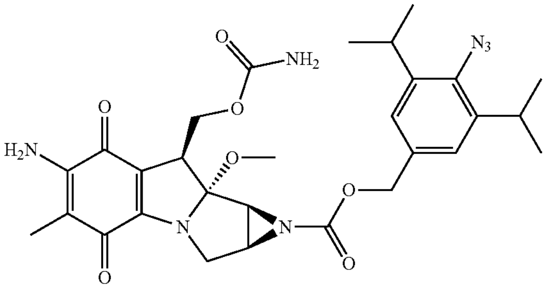 [SMILES: CO[C@@]12[C@H](COC(N)=O)C3=C(C(=O)C(C)=C(N)C3=O)N1C[C@H]1[C@@H]2N1C(=O)OCc1cc(C(C)C)c(N=[N+]=[N-])c(C(C)C)c1]

Specific examples of the present complex having doxorubicin as the leaving site include doxorubicin-ABC represented by the following chemical structural formula.

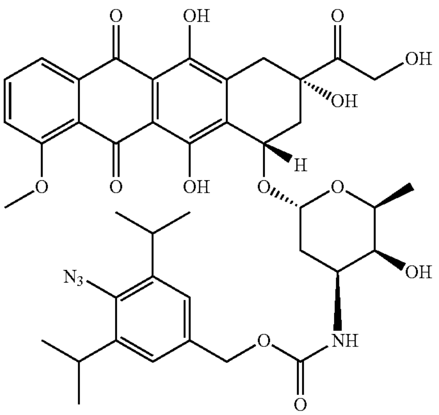 [SMILES: COc1cccc2c1C(=O)c1c(O)c3c(c(O)c1C2=O)C[C@@](O)(C(=O)CO)C[C@@H]3O[C@H]1C[C@H](NC(=O)OCc2cc(C(C)C)c(N=[N+]=[N-])c(C(C)C)c2)[C@H](O)[C@H](C)O1]

Specific examples of the present complex having dacarbazine as the leaving site include dacarbazine-ABC represented by the following chemical structural formula.

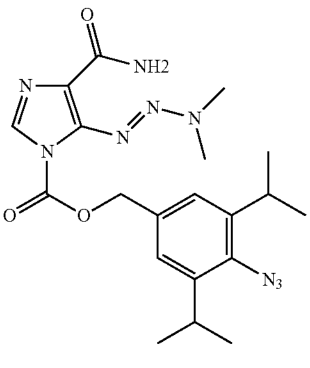 [SMILES: CC(C)c1cc(COC(=O)n2cnc(C(N)=O)c2/N=N/N(C)C)cc(C(C)C)c1N=[N+]=[N-]]

Specific examples of the present complex having crizotinib as the leaving site include crizotinib-ABC represented by the following chemical structural formula.

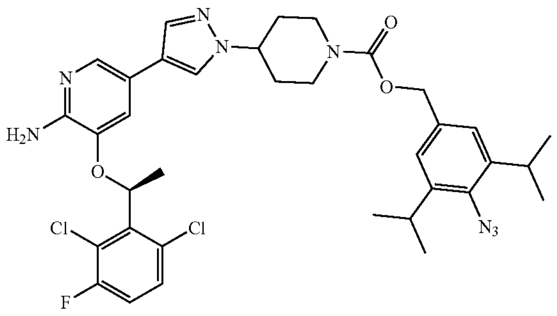 [SMILES: CC(C)c1cc(COC(=O)N2CCC(n3cc(-c4cnc(N)c(O[C@@H](C)c5c(Cl)ccc(F)c5Cl)c4)cn3)CC2)cc(C(C)C)c1N=[N+]=[N-]]

Specific examples of the present complex having endoxifen as the leaving site include endoxifen-ABC represented by the following chemical structural formula.

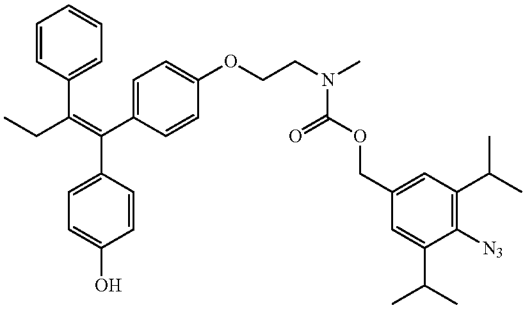 [SMILES: CC/C(=C(\c1ccc(O)cc1)c1ccc(OCCN(C)C(=O)OCc2cc(C(C)C)c(N=[N+]=[N-])c(C(C)C)c2)cc1)c1ccccc1]

Specific examples of the present complex having puromycin as the leaving site include puromycin-ABC represented by the following chemical structural formula.

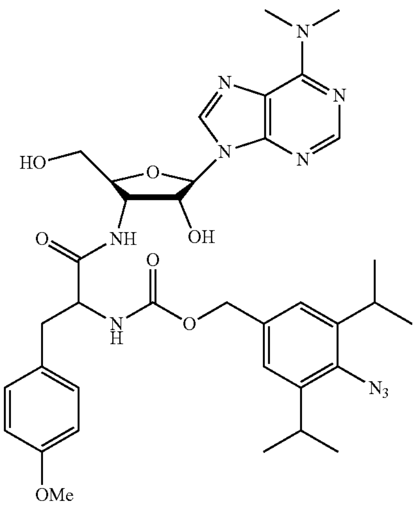

Labelled Compound

Examples of the labelled compound used as the leaving site include, but not limited to, a radioisotope, a fluorescent substance, an enzyme, and the like.

Specific examples of the labelled compound include: radioisotopes such as $^{3}H$, $^{14}C$, $^{125}I$, and $^{131}I$; fluorescent substances such as green fluorescent protein (GFP), fluorescein isothiocyanate, tetramethylrhodamine isothiocyanate, and $Eu^{3+}$; methylcoumarin-based compounds; and enzymes such as peroxidase, alkaline phosphatase, β-D-galactosidase, glucose oxidase, and glucose-6-phosphate dehydrogenase.

The present complex having a labelled compound as the leaving site can react with acrolein that is present around a tumor cell to release the labelled compound. Therefore, for example, the present complex can be used as a diagnostic drug for determining the presence or absence of a tumor, a size of a tumor, and for imaging of a tumor.

2. Method for Producing Complex

The following description will discuss a method for producing the present complex with reference to an example of the present complex in which the linker having the chemical structure represented by Formula (2) binds to a nitrogen atom in the leaving site (i.e., a carbamate bond is formed).

The present complex can be produced by any method that synthesizes a carbamate bond. Examples of such a method include a method for causing a reaction between isocyanate and alcohol, a method for causing a reaction between amine and carbonic acid ester, and the like.

The method for causing a reaction between isocyanate and alcohol is carried out, for example, as follows: in the presence of an appropriate solvent, an amino group of a compound used as the leaving site is caused to react with triphosgene to obtain isocyanate; and then the resulting isocyanate is caused to react with alcohol represented by Formula (5) to produce the present complex in which a carbamate bond is formed.

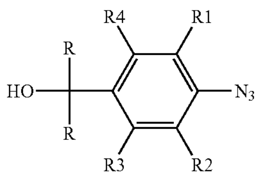

(5)

The method for causing a reaction between amine and carbonic acid ester is carried out, for example, as follows: in the presence of an appropriate solvent, alcohol represented by Formula (5) is caused to react with chloroformic ester to obtain carbonic acid ester; and then the resulting carbonic acid ester is caused to react with an amino group of a compound used as the leaving site to produce the present complex in which a carbamate bond is formed.

For the method for producing the present complex, it is also possible to refer to the descriptions of Examples and the descriptions of ACS Sens. 2016, 1, 623-632 (Non-patent Literature 5).

3. Therapeutic Agent for Tumor

A therapeutic agent for a tumor in accordance with an embodiment of the present invention (hereinafter simply referred to also as "present therapeutic agent") contains, as an active ingredient, the present complex in which the leaving site is an antitumor compound.

Other Components

The present therapeutic agent may contain, in addition to the present complex, a pharmaceutically acceptable carrier to an extent that does not inhibit activity of the present complex. Examples of such a carrier include water, an electrolyte liquid, a sugar solution, and the like.

The present therapeutic agent may contain an adjuvant. Examples of such an adjuvant include a buffer, a soothing agent, a stabilizer, a preservative, an antioxidant, a colorant, and the like.

Examples of the buffer include buffer solutions such as phosphate, acetate, carbonate, and citrate.

Examples of the soothing agent include propylene glycol, lidocaine hydrochloride, benzyl alcohol, benzalkonium chloride, procaine hydrochloride, and the like.

Examples of the stabilizer include human serum albumin, polyethylene glycol, and the like.

Examples of the preservative include benzyl alcohol, phenol, and the like.

Examples of the antioxidant include sulfite, ascorbate, and the like.

Suitable examples of the colorant include water-soluble coloring tar dyes (e.g., food dyes such as food red No. 2 and No. 3, food yellow No. 4 and No. 5, and food blue No. 1 and No. 2), insoluble lake dyes (e.g., aluminum salts of the above water-soluble edible tar dyes), natural dyes (e.g., β-carotene, chlorophyll, bengala), and the like.

The present therapeutic agent may contain additives such as a binder, an excipient, a lubricant, a sweetening agent, a flavoring agent, a preservative, a disintegrant, a suspending agent, a solvent, a solubilizing agent, an isotonizing agent, and an expanding agent.

Examples of the binder include gelatin, cornstarch, traganth, gum arabic, pregelatinized starch, sucrose, methylcellulose, carboxymethylcellulose, sodium carboxymethylcellulose, crystalline cellulose, white sugar, D-mannitol, trehalose, dextrin, pullulan, hydroxypropylcellulose, hydroxypropylmethylcellulose, polyvinylpyrrolidone, and the like.

Excipients include lactose, white sugar, D-mannitol, D-sorbitol, starch, pregelatinized starch, dextrin, crystalline cellulose, low-substituted hydroxypropylcellulose, sodium carboxymethylcellulose, gum arabic, pullulan, soft silicic acid anhydride, synthetic aluminum silicate, magnesium aluminometasilicate, xylitol, sorbitol, erythritol, and the like.

Examples of the lubricant include magnesium stearate, calcium stearate, talc, colloidal silica, polyethylene glycol, and the like.

Examples of the sweetening agent include saccharin sodium, dipotassium glycyrrhizinate, aspartame, *stevia*, and the like.

Examples of the flavoring agent include peppermint, *Gaultheria adenothrix* oil, cherry, and the like.

Examples of the preservative include parahydroxybenzoates, chlorobutanol, benzyl alcohol, phenethyl alcohol, dehydroacetic acid, sorbic acid, and the like.

Examples of the disintegrant include lactose, white sugar, starch, carboxymethylcellulose, carboxymethylcellulose calcium, croscarmellose sodium, carboxymethylstarch sodium, low-substituted hydroxypropylcellulose, soft silicic acid anhydride, calcium carbonate, and the like.

Examples of the suspending agent include surfactants such as, for example, stearyl triethanolamine, sodium lauryl sulfate, lauryl aminopropionic acid, lecithin, benzalkonium chloride, benzethonium chloride, and glycerol monostearate; hydrophilic polymers such as, for example, polyvinyl alcohol, polyvinylpyrrolidone, sodium carboxymethylcellulose, methylcellulose, hydroxymethylcellulose, hydroxyethylcellulose, and hydroxypropylcellulose; polysorbates; polyoxyethylene hydrogenated castor oil; and the like.

Suitable examples of the solvent include injectable water, physiological saline solution, Ringer's solution, alcohol, propylene glycol, polyethylene glycol, sesame oil, corn oil, olive oil, cottonseed oil, and the like.

Suitable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate, and the like.

Suitable examples of the isotonizing agent include sodium chloride, glycerine, D-mannitol, D-sorbitol, glucose, xylitol, fructose, and the like.

Dosage Form

The present therapeutic agent can be administered as an oral formulation, an injectable formulation, or a transdermal formulation. Examples of the oral formulation include tablets (including a sublingual tablet and an orally disintegrating agent), capsules (including a soft capsule and a microcapsule), powder, a granule, a troche, a syrup, an emulsion, a suspension, and the like. Examples of the injectable formulation include intradermal injection, subcutaneous injection, intravenous injection, intramuscular injection, intraspinal injection, epidural injection, local injection, and the like. Furthermore, examples of the transdermal formulation include a patch, an ointment, and an epispastic. These formulations may be controlled-release formulations such as quick-release formulations or sustained-release formulations (e.g., a sustained-release microcapsule).

Production Method

The present therapeutic agent is suitably formulated as an injectable formulation. An aseptic composition for the injectable formulation can be formulated in accordance with general formulation practice, such as dissolving or suspending an active substance in a vehicle (aqueous solution for injection; naturally-produced vegetable oil such as sesame oil and palm oil). As the aqueous solution for injection, it is possible to use, for example, a physiological saline solution, an isotonic solution containing glucose or another adjuvant (e.g., D-sorbitol, D-mannitol, sodium chloride, or the like). The aqueous solution for injection may be used in combination with a suitable solubilizing agent, for example, alcohol (e.g., ethanol), polyalcohol (e.g., propylene glycol, polyethylene glycol), a non-ionic surfactant (e.g., polysorbate 80TM, HCO-50), or the like. As an oil solution, for example, a sesame oil, a soybean oil, or the like is used, and the oil solution may be used in combination with a solubilizing agent such as benzyl benzoate or benzyl alcohol. The injectable formulation can be enclosed in a container such as an ampule or a vial in a unit dose or in a multiple-dose. Furthermore, it is possible that an active ingredient and a pharmaceutically acceptable carrier are lyophilized and stored in a state that only needs to be dissolved or suspended in an appropriate aseptic vehicle immediately before use.

Contained Amount of Present Complex

An amount of the present complex contained in the present therapeutic agent differs according to the form of formulation. The amount is usually approximately 10% by mass to 25% by mass, preferably not less than approximately 15% by mass, and more preferably not less than approximately 20% by mass, relative to the entire formulation.

Dose

A dose of the present therapeutic agent can be determined appropriately while taking into consideration a type of administration subject, a method of administration, a type of antitumor agent, a type of tumor cell, a site, and the like. In a case where the administration is intravenous administration to a human solid cancer, the amount of the present complex per kilogram of body weight is preferably 2 mg to 5 mg, more preferably not less than 3 mg, and further preferably not less than 4 mg. These effective doses can each be administered in a single time or in several times.

Administration Subject

The present therapeutic agent can be applied to any mammalian tumor. A type of mammal may be a non-human mammal or a human. Examples of the non-human mammals include: experimental animals such as rodents (such as a mouse, a rat, a hamster, and a guinea pig) and a rabbit; domestic animals such as a pig, a cattle, a goat, a horse, a sheep, and a mink; pets such as a dog and a cat; a human; primates (excluding humans) such as a monkey, a rhesus monkey, a marmoset, an orangutan, and a chimpanzee; and the like.

The administration subject of the present therapeutic agent is any of the above subjects that has a tumor. Examples of a type of tumor include, but not particularly limited to: lung cancer (e.g., lung adenocarcinoma), uterine cancer (e.g., cervical cancer, uterine body cancer), gastric cancer, colon cancer, rectal cancer, pancreatic cancer, liver cancer, gallbladder cancer, bile duct cancer, breast cancer, bladder tumor, osteosarcoma, malignant melanoma, pheochromocytoma, and the like.

4. Method for Causing Leaving Site to Leave Present Complex or Present Therapeutic Agent A method for causing a leaving site to leave the present complex or the present therapeutic agent (hereinafter simply referred to also as "present method") in accordance with an embodiment of the present invention includes a step of causing the present complex or the present therapeutic agent to react with acrolein.

Acrolein that reacts with the present complex or the present therapeutic agent may be present in vivo or may be present in vitro.

In a case of reacting with acrolein that is present in vivo, the present method can be applied to any mammal. A type of mammal may be a non-human mammal or a human. Examples of the non-human mammals include: experimental animals such as rodents (such as a mouse, a rat, a hamster, and a guinea pig) and a rabbit; domestic animals such as a pig, a cattle, a goat, a horse, a sheep, and a mink; pets such as a dog and a cat; a human; primates (excluding humans) such as a monkey, a rhesus monkey, a marmoset, an orangutan, and a chimpanzee; and the like.

5. Main Points of Embodiment

Embodiments of the present invention include, for example, aspects described below.

<1> A complex containing: an acrolein-reactive site having a chemical structure represented by Formula (1); and a leaving site having another chemical structure, the leaving site binding to the acrolein-reactive site via a linker that is cleavable by a reaction between the acrolein-reactive site and acrolein, (1)

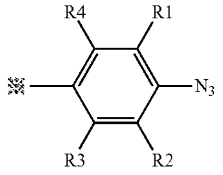

wherein

R1 and R2 each independently represent a hydrogen atom, a halogen atom, or an alkyl group that has 1 to 5 carbon atoms and that may be substituted by at least one halogen atom, provided that at least one of R1 and R2 is the alkyl group having 1 to 5 carbon atoms;

R3 and R4 each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms (provided that a hydrogen atom constituting the alkyl group may be substituted by a substituent selected from a halogen atom, a hydroxy group, and an amino group that may have a substituent); and ※※ is a binding site to the linker.

<2> The complex described in <1>, in which the linker is a linker having a chemical structure represented by Formula (2):

(2)

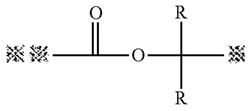

wherein two R each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms (provided that a hydrogen atom constituting the alkyl group may be substituted by a substituent selected from a halogen atom, a hydroxy group, and an amino group that may have a substituent);

※※ is a binding site to the acrolein-reactive site; and

※※ is a binding site to the leaving site.

<3> The complex described in <2>, in which: ※※ in Formula (2) is a binding site to a nitrogen atom, a sulfur atom, or an oxygen atom contained in the leaving site.

<4> The complex described in <2> or <3>, in which: two R in Formula (2) each independently represent a hydrogen atom, a halogen atom, or an alkyl group having 1 to 5 carbon atoms (provided that a hydrogen atom constituting the alkyl group may have a substituent selected from a halogen atom, a hydroxy group, and an amino group that may have a substituent).

<5> The complex described in any one of <1> through <4>, in which: R1 and R2 in Formula (1) each independently represent an alkyl group that has 1 to 5 carbon atoms and that may be substituted by at least one halogen atom.

<6> The complex described in any one of <1> through <5>, in which: the leaving site is an antitumor compound.

<7> The complex described in any one of <1> through <6>, in which: the leaving site leaves by reacting with acrolein that is present around a tumor cell.

<8> A therapeutic agent for a tumor, the therapeutic agent containing the complex described in <6> or <7>.

<9> A method for causing a leaving site to leave, the method including the step of: causing the complex described in any one of <1> through <7> or the therapeutic agent described in <8> to react with acrolein.

The present invention is not limited to the embodiments, but can be altered by a skilled person in the art within the scope of the claims. The present invention also encompasses, in its technical scope, any embodiment derived by combining technical means disclosed in differing embodiments.

EXAMPLES

Chemical Synthesis

All chemically available reagents were used without further purification. Preparative separation was carried out by column chromatography on Merck Silica gel 60 (230-400 mesh). $^{1}H$ and $^{13}C$ NMR spectra were recorded with use of a JEOL RESONANCE AL400 NMR spectrometer. Unless otherwise mentioned, $CDCl_3$ was used as a solvent. Chemical shifts were represented as 6-values relative to the internal standard TMS. High-resolution mass spectrometry (HRMS) was recorded on micrOTOF-QIII. Fluorescence spectra were measured with use of a spectrofluorometer (SpectraMax iD3, manufactured by Molecular Devices). Azide-containing compounds are presumed to be potentially explosive. Therefore, all manipulations were carefully carried out in a hood.

[Production Example 1] Synthesis of 2,6-diisopropylphenylazide (Compound 1)

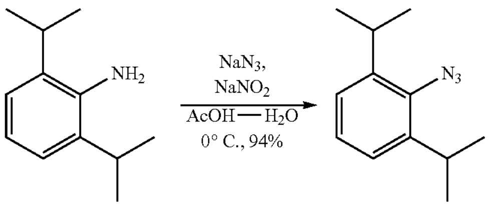

2,6-diisopropylaniline

1

To a mixture of 2,6-diisopropylaniline (846 mg, 4.77 mmol, 1.0 eq) and sodium azide (791 mg, 11.9 mmol, 2.5 eq) dissolved in acetic acid and distilled water (9:1) (50 mL,

[2,6-diisopropylaniline]=0.1 M) was slowly added sodium nitrite (814 mg, 11.5 mmol, 2.4 eq) at 0 °C. After stirring for 30 minutes at 0 °C, a saturated aqueous solution of $NaHCO_3$ was added until the mixture became pH 7. The mixture was extracted with EtOAc. The combined organic phase was washed with brine, dried over $Na_2SO_4$, and filtered. The filtrate was concentrated to dryness under reduced pressure. The residue was purified by column chromatography on silica gel (n-hexane only) to obtain intended 2,6-diisopropylphenylazide (compound 1) as a yellow oil (912 mg, 94%). $^1H$ NMR (400 MHz, $CDCl_3$, 25 °C) δ 7.25-7.07 (m, 3H), 3.36 (hept, J=7.0 Hz, 2H), 1.26 (d, J=6.8 Hz, 12H); $^{13}C$ NMR (100 MHz, $CDCl_3$, 25 °C) δ 143.33, 135.54, 127.01, 124.12, 28.91, 23.59.

[Production Example 2] Reaction Between 2,6-diisopropylphenylazide (Compound 1) and Acrolein

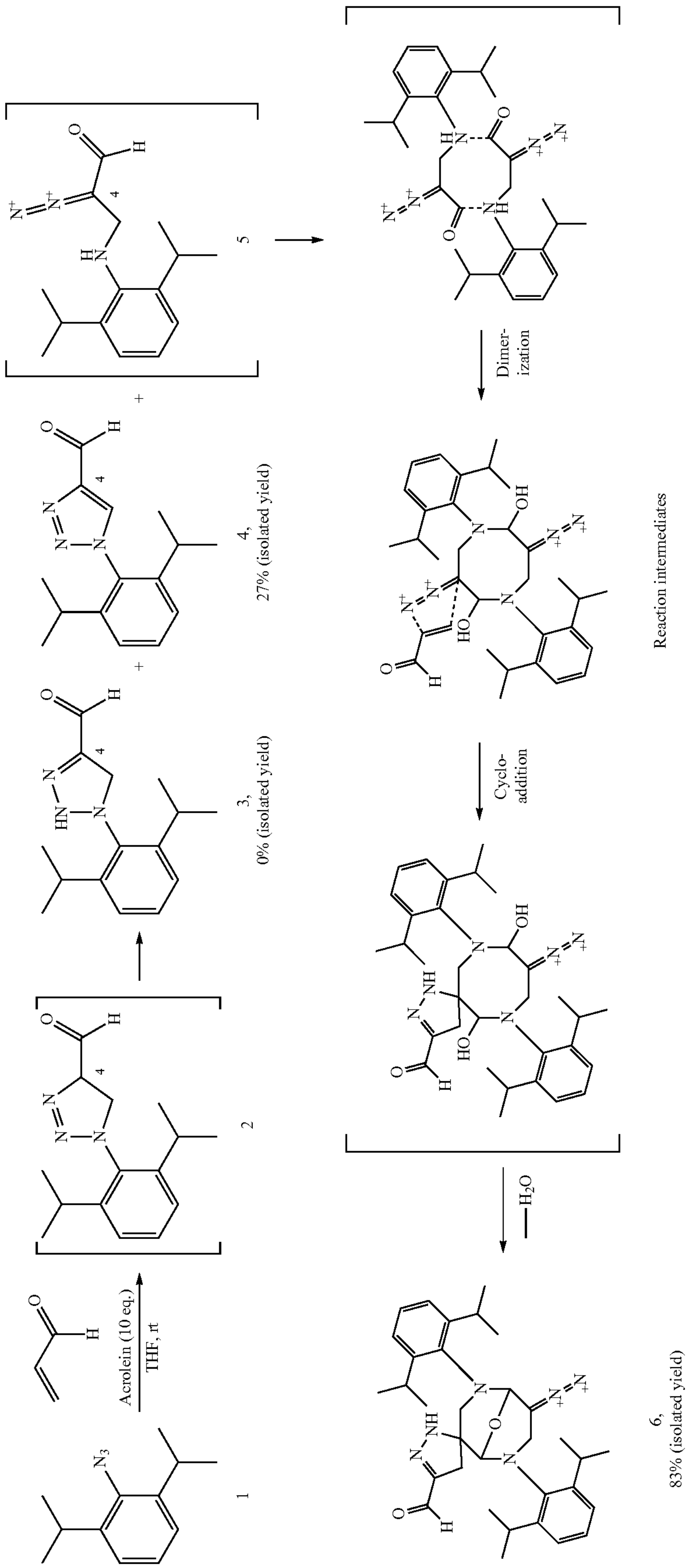
Acrolein (10 eq.)
THF, rt
1
2
3,
0% (isolated yield)
4,
27% (isolated yield)
5
Dimer-
ization
Cyclo-
addition
Reaction intermediates
—H2O
6,
83% (isolated yield)

To a solution of 2,6-diisopropylphenylazide (compound 1) (47.3 mg, 0.23 mmol, 1.0 eq) in THF (stabilizer free, 310 μL, [compound 1]=0.7 M) was added acrolein (164 μL, 2.33 mmol, 10 eq). After being stirred at room temperature for 24 hours, the reaction mixture was concentrated to dryness under reduced pressure. The resulting crude product was purified by preparative TLC (n-hexane/ethyl acetate=3:1) to obtain 4-formyl-1,2,3-triazole (compound 4) (Rf value of 0.66, 27%, yellow oil) and heterocycle (compound 6) (Rf value of 0.42, 53%, red oil). 4-formyl-1,2,3-triazole (compound 4): $^1H$ NMR (400 MHz, $CDCl_3$, 25 °C) δ 10.29 (s, 1H), 8.19 (s, 1H), 7.54 (t, J=7.8 Hz, 1H), 7.33 (d, J=7.8 Hz, 2H), 2.16 (hept, J=6.9 Hz, 2H), 1.14 (dd, J=10.4, 6.8 Hz, 12H); $^{13}C$ NMR (100 MHz, $CDCl_3$, 25 °C) δ 185.60, 145.97, 131.65, 128.19, 124.27, 28.63, 24.17, 24.02; ESI-HRMS m/z calculated for $C_{15}H_{19}N_3NaO$ ($[M+Na]^+$) 280.1420, found 280.1419.

Heterocycle (compound 6): $^1H$ NMR (400 MHz, $CDCl_3$, 25 °C) δ 9.38 (s, 1H), 7.38 (t, J=7.7 Hz, 1H), 7.29 (t, J=7.7 Hz, 1H), 7.22 (d, J=7.7 Hz, 2H), 7.15 (dd, J=7.6, 3.1 Hz, 2H), 5.85 (s, 1H), 5.54 (s, 1H), 4.20 (q, J=26.3 Hz, 2H), 4.11 (d, J=11.0 Hz, 1H), 3.31 (d, J=11.0 Hz, 1H), 3.12 (s, 2H), 2.94 (p, J=6.9 Hz, 1H), 2.83 (p, J=7.1 Hz, 3H), 1.23-1.18 (m, 24H); $^{13}C$ NMR (100 MHz, $CDCl_3$, 25 °C) δ 189.33, 147.46, 146.89, 143.09, 140.10, 134.52, 129.87, 128.57, 124.37, 124.32, 120.59, 109.18, 92.90, 84.51, 53.37, 51.37, 39.40, 28.76, 28.23, 28.17, 24.78, 24.71, 24.68, 24.48; ESI-HRMS m/z calculated for $C_{33}H_{45}N_6O_2$ ($[M+H]^+$) 557.3599, found 557.3597.

[Production Example 3] Synthesis of Coumarin-ABC (Compound 7) (Fluorochrome-ABC)

Coumarin-ABC (compound 7) is synthesized in Production Example 3 along a route as shown below.

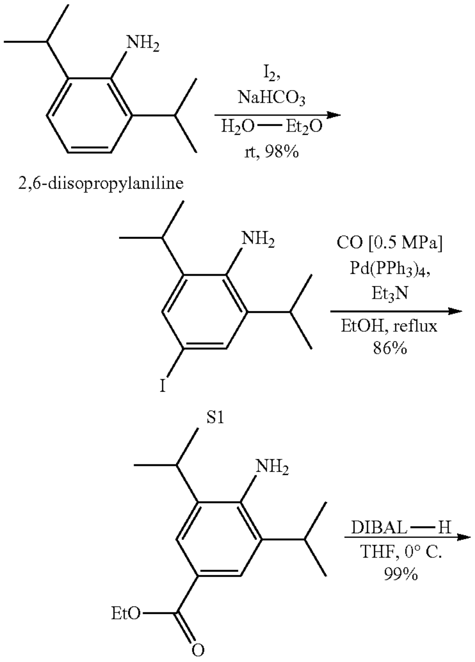

2,6-diisopropylaniline

S1

S2

-continued

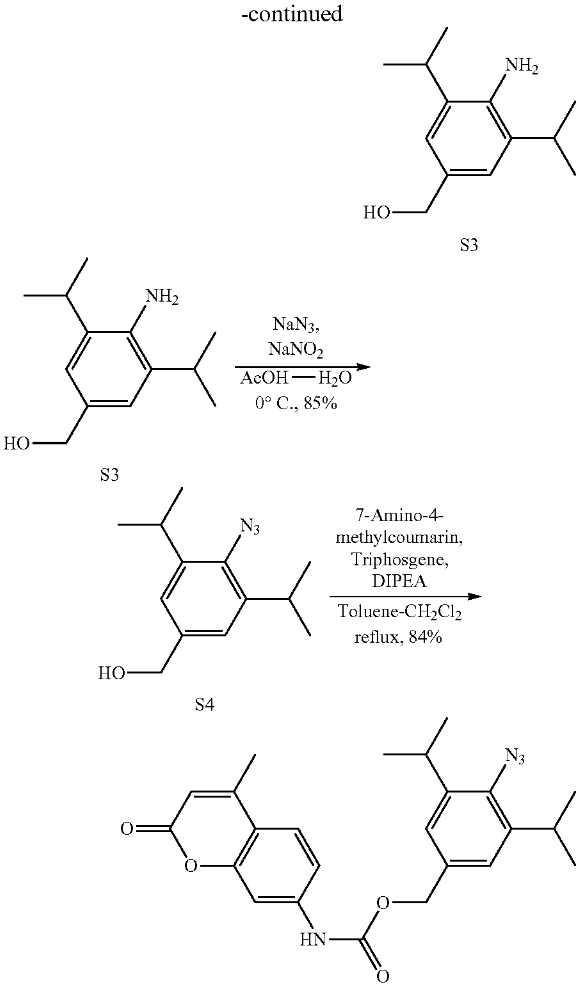

S3

S3

S4

7

The following description will discuss details of each process.

(Production Example 3-1) Synthesis of 4-iodo-2,6-diisopropylaniline (Compound S1)

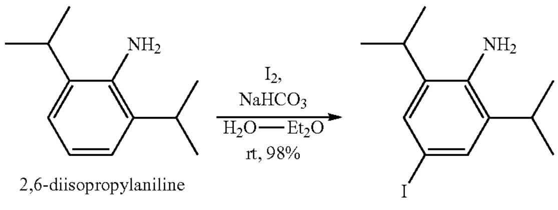

2,6-diisopropylaniline

S1

To a solution of 2,6-diisopropylaniline (8.8 g, 44.9 mmol, 1.0 eq) in a saturated aqueous solution of $NaHCO_3$ and $Et_2O$ (1:1) (200 mL, [2,6-diisopropylaniline]=0.2 M) was added iodine (13.7 g, 53.8 mmol, 1.2 eq). After being stirred for 5 hours at room temperature, $Na_2S_2O_3 \cdot H_2O$ was added, and the mixture was stirred for 15 minutes. The resulting mixture was extracted with $Et_2O$. The combined organic phase was washed with brine, dried over $Na_2SO_4$, and filtered. The filtrate was concentrated to dryness under reduced pressure to obtain intended 4-iodo-2,6-diisopropylaniline (compound S1) as red-black oil (13.4 g, 98%). $^{1}$H NMR (400 MHz, $CDCl_3$, 25 °C) δ 7.27 (s, 2H), 3.70 (bs, 2H, NH2), 2.81 (hept, J=6.7 Hz, 2H), 1.21 (d, J=6.8 Hz, 12H); $^{13}$C NMR (100 MHz, $CDCl_3$, 25 °C) δ 140.27, 135.08, 131.79, 81.12, 27.82, 22.21; ESI-HRMS m/z calculated for $C_{12}H_{19}IN$ ($[M+H]^+$) 304.0557, found 304.0558.

(Production Example 3-2) Synthesis of Ethyl 4-amino-3,5-diisopropylbenzoate (Compound S2)

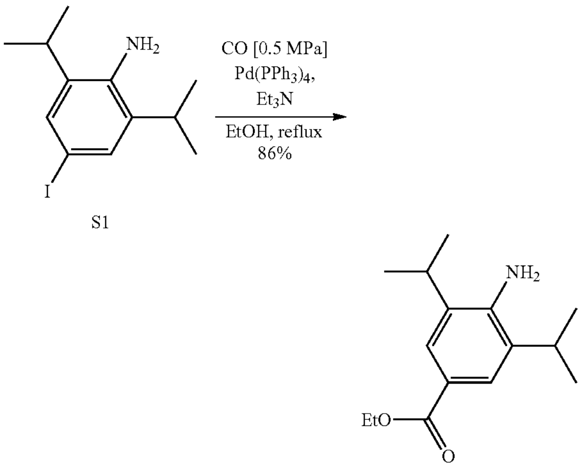

S1

S2

To a mixture of 4-iodo-2,6-diisopropylaniline (compound S1) (6.2 g, 20.5 mmol, 1.0 eq) and $Pd(PPh_3)_4$ (0.5 g, 0.41 mmol, 0.02 eq) in EtOH (17 mL, [S1]=1.2 M) was added $Et_3N$ (4.3 mL, 30.7 mmol, 1.5 eq). The resulting solution was stirred under CO pressure (0.5 MPa) at 110 °C for 8 hours. The suspension was filtered through Celite and the filtrate was concentrated to dryness under reduced pressure. The residue was purified by column chromatography on silica gel using a gradient of eluents [n-hexane/ethyl acetate (25:1 to 15:1)] to obtain intended ethyl 4-amino-3,5-diisopropylbenzoate (compound S2) as yellow oil (4.4 g, 86%). $^{1}$H NMR (400 MHz, $CDCl_3$, 25 °C) δ 7.75 (s, 2H), 4.34 (q, J=7.1 Hz, 2H), 4.16 (bs, 2H, NH2), 2.88 (hept, J=6.9 Hz, 2H), 1.38 (t, J=7.2 Hz, 3H), 1.29 (d, J=6.8 Hz, 12H); $^{13}$C NMR (100 MHz, $CDCl_3$, 25 °C) δ 167.64, 145.10, 131.37, 125.04, 119.77, 60.30, 27.97, 22.24, 14.55; ESI-HRMS m/z calculated for $C_{15}H_{24}NO_2$ ($[M+H]^+$) 250.1802, found 250.1805.

(Production Example 3-3) Synthesis of 4-hydroxymethyl-2,6-diisopropylaniline (Compound S3)

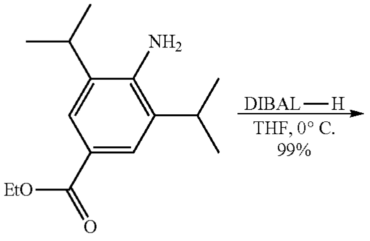

S2

-continued

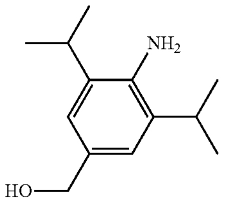

S3

To a solution of ethyl 4-amino-3,5-diisopropylbenzoate (compound S2) (764 mg, 3.1 mmol, 1.0 eq) in THF (30 mL, [S2]=0.1 M) at 0 °C was slowly added DIBAL-H (9 mL of a 1.0 M solution in toluene, 9.2 mmol, 3.0 eq). The reaction liquid was stirred under nitrogen atmosphere at 0 °C for 10 minutes, and then for 1 hour at room temperature. The excess DIBAL-H was quenched carefully with MeOH (20 mL) at 0 °C, stirred for 30 minutes, and allowed to warm to room temperature. The resulting mixture was filtered through Celite (washed with MeOH), and the filtrate was concentrated to dryness under reduced pressure. The residue was purified by column chromatography on silica gel using a gradient of eluents [n-hexane/ethyl acetate (15:1 to 7:1)] to obtain intended 4-hydroxymethyl-2,6-diisopropylaniline (compound S3) as an orange oil (627 mg, 99%). $^{1}$H NMR (400 MHz, $CDCl_3$, 25 °C) δ 7.04 (s, 2H), 4.55 (s, 2H), 3.74 (bs, 2H, NH2), 2.92 (hept, J=6.7 Hz, 2H), 1.27 (d, J=6.8 Hz, 12H); $^{13}$C NMR (100 MHz, $CDCl_3$, 25 °C) δ 140.06, 132.71, 130.89, 122.46, 66.09, 27.99, 22.44; ESI-HRMS m/z calculated for $C_{13}H_{22}NO_2$ ($[M+H]^+$) 208.1696, found 208.1699.

(Production Example 3-4) Synthesis of (4-azido-3, 5-diisopropylphenyl)-methanol (Compound S4)

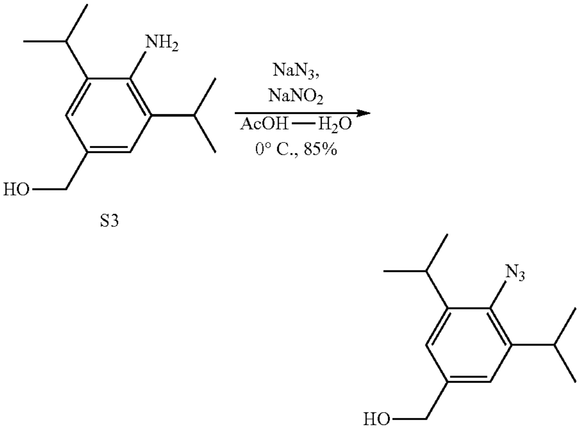

S3

S4

To a mixture of 4-hydroxymethyl-2,6-diisopropylaniline (compound S3) (763 mg, 3.68 mmol, 1.0 eq) and sodium azide (610 mg, 9.20 mmol, 2.5 eq) dissolved in acetic acid and distilled water (5:2) (35 mL, [S3]=0.1 M) was slowly added sodium nitrite (628 mg, 8.83 mmol, 2.4 eq) at 0 °C. After stirring for 4 hours at 0 °C, a saturated aqueous solution of $NaHCO_3$ was added until the mixture became pH 7. The mixture was extracted with EtOAc. The combined organic phase was washed with brine, dried over $Na_2SO_4$, and filtered. The filtrate was concentrated to dryness under reduced pressure. The residue was purified by column chromatography on silica gel using a gradient of eluents [n-hexane/ethyl acetate (30:1 to 15:1)] to obtain intended (4-azido-3,5-diisopropylphenyl)-methanol (compound S4) as a yellow oil (730 mg, 85%). $^{1}H$ NMR (400 MHz, $CDCl_3$, 25 °C) δ 7.13 (s, 2H), 4.64 (s, 2H), 3.36 (p, J=6.8 Hz, 2H), 1.27 (d, J=6.7 Hz, 12H); $^{13}C$ NMR (100 MHz, $CDCl_3$, 25 °C) δ 143.51, 139.31, 134.84, 122.79, 65.27, 28.90, 23.52; ESI-HRMS m/z calculated for $C_{13}H_{20}N_3O$ ($[M+H]^+$) 234.1601, found 234.1605.

(Production Example 3-5) Synthesis of Coumarin-ABC (Compound 7)

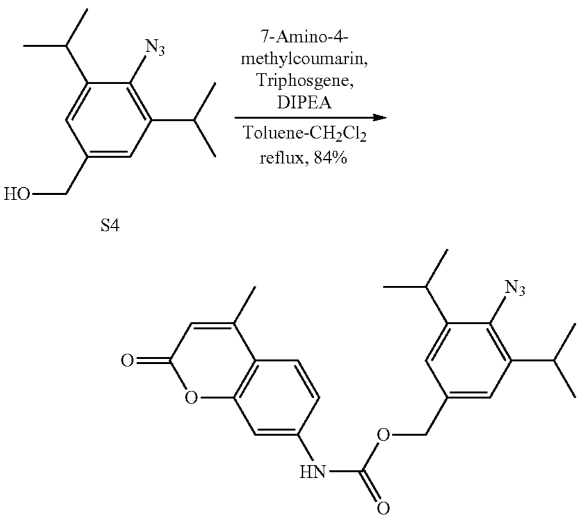

S4

7

To a mixture of 7-amino-4-methylcoumarin (69 mg, 0.39 mmol, 1.0 eq) and DIPEA (250 μL, 1.45 mmol, 3.8 eq) dissolved in toluene (4 mL, [7-amino-4-methylcoumarin] =0.1 M) at 0 °C was slowly added triphosgene (140 mg, 0.46 mmol, dissolved in 4 mL toluene). The reaction mixture was refluxed under nitrogen atmosphere for 4 hours, and then cooled to room temperature. To the reaction mixture, $CH_2Cl_2$ (3 mL) was added and stirred for 5 minutes until the solution turned into dark brown, and compound S4 (117 mg, 0.5 mmol, 1.3 eq, in 5 mL $CH_2Cl_2$) was added. The reaction mixture was stirred and heated at 55 °C for 13 hours, and then cooled to room temperature. The resulting solution was concentrated to dryness under reduced pressure while maintaining the temperature at 30 °C. The residue was purified by column chromatography on silica gel ($CHCl_3$/MeOH 25:1) to obtain intended coumarin-ABC (compound 7) as pale yellow solid (141 mg. 84%). $^{1}H$ NMR (400 MHz, DMSO-d6, 25 °C) δ 10.28 (bs, 1H, NH), 7.69 (d, J=8.7 Hz, 1H), 7.55 (d, J=2.1 Hz, 1H), 7.41 (dd, J=8.7, 2.0 Hz, 1H), 7.31 (s, 2H), 6.23 (d, J=1.4 Hz, 1H), 5.15 (s, 2H), 3.29 (p, J=6.9 Hz, 2H), 2.38 (d, J=1.3 Hz, 3H), 1.22 (d, J=6.9 Hz, 12H); $^{13}C$ NMR (100 MHz, DMSO-d6, 25 °C) δ 160.17, 153.98, 153.33, 153.27, 142.84, 142.81, 134.90, 134.49, 126.17, 124.60, 114.51, 114.35, 112.03, 104.53, 66.29, 28.39, 23.29, 17.99; ESI-HRMS m/z calculated for $C_{24}H_{26}N_4NaO_4$ ($[M+Na]^+$) 457.1846, found 457.1840.

[Production Example 4] Synthesis of Prodrug MMC-ABC (Compound 8) (Drug-ABC)

MMC-ABC (compound 8) is synthesized in Production Example 4 along a route as shown below.

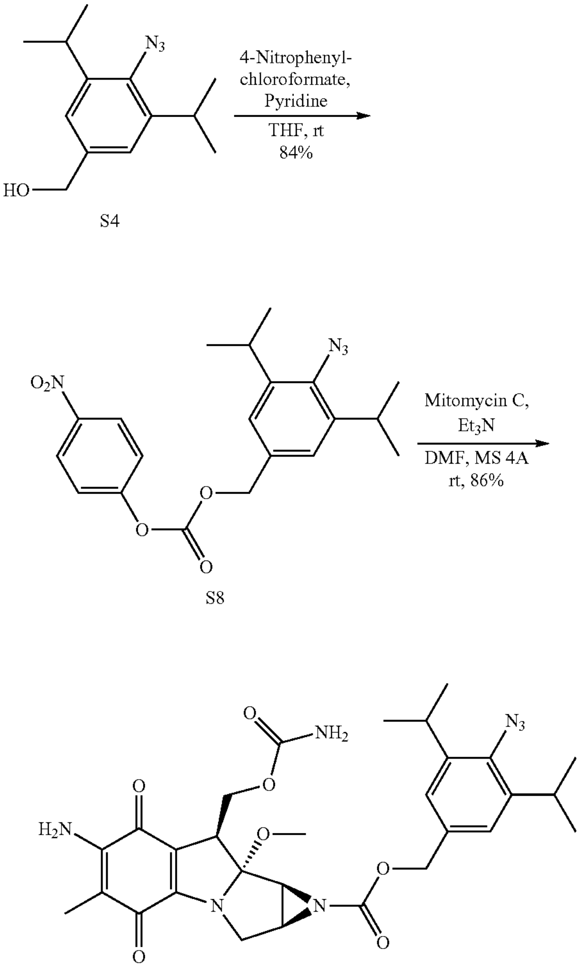

S4

S8

8

The following description will discuss details of each process.

(Production Example 4-1) Synthesis of 4-azido-3,5-diisopropylbenzyl-(4-nitrophenyl)-carbonate (Compound S5)

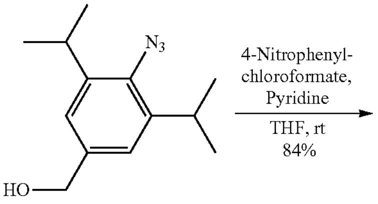

S4

-continued

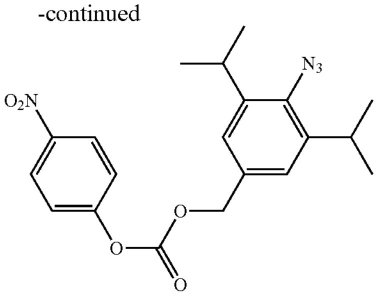

S5

To a mixture of compound S4 (297 mg, 1.27 mmol, 1.0 eq) and 4-nitrophenyl chloroformate (321 mg, 1.53 mmol, 1.2 eq) dissolved in THF (13 mL, [S4]=0.1 M) at 0 °C was added pyridine (206 μL, 2.55 mmol, 2.0 eq). The reaction mixture was stirred under nitrogen atmosphere at room temperature for 24 hours. The THF was removed by a rotary evaporator, and the resulting crude was partitioned with use of EtOAc-$H_2O$. The combined organic phase was washed with brine, dried over $Na_2SO_4$, and filtered. The filtrate was concentrated to dryness under reduced pressure. The residue was purified by column chromatography on silica gel (n-hexane/ethyl acetate 25:1) to obtain intended 4-azido-3, 5-diisopropylbenzyl-(4-nitrophenyl)-carbonate (compound S5) as a yellow oil (424 mg, 84%). $^1$H NMR (400 MHz, $CDCl_3$, 25 °C) δ 8.27 (d, J=9.1 Hz, 2H), 7.20 (s, 2H), 5.26 (s, 2H), 3.38 (p, J=6.9 Hz, 2H), 1.29 (d, J=6.9 Hz, 12H); $^{13}$C NMR (100 MHz, $CDCl_3$, 25 °C) δ 155.65, 152.50, 145.52, 143.82, 136.11, 132.62, 125.41, 124.63, 121.86, 71.07, 28.94, 23.53.

(Production Example 4-2) Synthesis of Prodrug MMC-ABC (Compound 8)

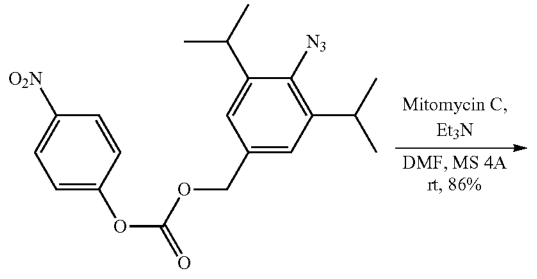

S5

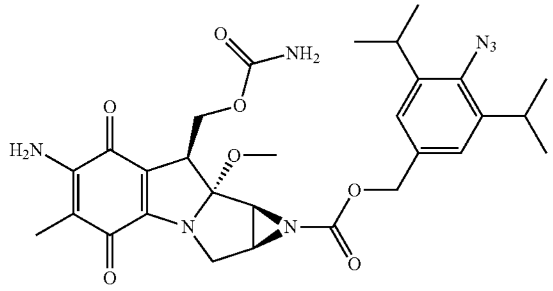

8

To a mixture of compound S5 (307 mg, 0.77 mmol, 1.0 eq), mitomycin C (170 mg, 0.51 mmol, 1.5 eq), and activated powder molecular sieves (MS 4A) dissolve in DMF (8 mL, [S5]=0.1 M) was added $Et_3N$ (130 μL, 0.93 mmol, 1.8 eq). The reaction mixture was stirred under nitrogen atmosphere at room temperature for 16 hours. The resulting mixture was filtered through Celite (washed with EtOAc), and the filtrate was concentrated to dryness under reduced pressure. The resulting crude was partitioned with use of EtOAc-$H_2O$. The combined organic phase was washed with brine, dried over $Na_2SO_4$, and filtered. The filtrate was concentrated to dryness under reduced pressure. The residue was purified by column chromatography on silica gel ($CHCl_3$/MeOH 30:1) to obtain intended prodrug MMC-ABC (compound 8) as a purple oil (260 mg, 86%). $^1$H NMR (400 MHz, $CDCl_3$, 25 °C) δ 7.12 (s, 2H), 5.25 (bs, 2H, NH2), 5.04 (s, 2H), 4.89 (dd, J=10.8, 4.7 Hz, 1H), 4.73 (bs, 2H, NH2), 4.44 (d, J=13.3 Hz, 1H), 4.32 (t, J=11.0 Hz, 1H), 3.70 (dd, J=11.0, 4.8 Hz, 1H), 3.48 (dd, J=13.3, 1.9 Hz, 1H), 3.45 (d, J=4.6 Hz, 1H), 3.37-3.27 (m, 3H), 3.19 (s, 3H), 1.76 (s, 3H), 1.25 (dd, J=6.9, 4.1 Hz, 12H); $^{13}$C NMR (100 MHz, $CDCl_3$, 25 °C) δ 178.53, 176.03, 160.82, 156.46, 154.47, 147.15, 143.52, 135.60, 133.83, 124.67, 110.67, 105.58, 105.31, 68.80, 62.29, 49.90, 48.81, 43.52, 42.01, 40.21, 28.93, 23.55, 8.01; ESI-HRMS m/z calculated for $C_{29}H_{36}N_7O_7$ ([M+H]$^+$) 594.2671, found 594.2673.

[Production Example 5] Synthesis of Control Compound 2-azido-1,3-diisopropyl-5-methylbenzene (Compound 9)

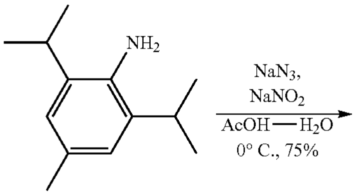

4-Methyl-2,6-diisopropylaniline

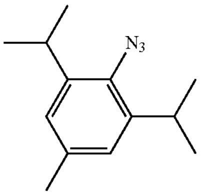

9

To a mixture of 4-methyl-2,6-diisopropylaniline (0.8 g, 4.18 mmol, 1.0 eq) and sodium azide (0.7 g, 10.5 mmol, 2.5 eq) dissolved in acetic acid and distilled water (5:2) (21 mL, [4-methyl-2,6-diisopropylaniline]=0.2 M) was slowly added sodium nitrite (0.7 mg, 10.0 mmol, 2.4 eq) at 0 °C. After stirring for 3 hours at 0 °C, a saturated aqueous solution of $NaHCO_3$ was added until the mixture became pH 7. The mixture was extracted with ethyl acetate. The combined organic phase was washed with brine, dried over $Na_2SO_4$, and filtered. The filtrate was concentrated to dryness under reduced pressure. The residue was purified by column chromatography on silica gel (n-hexane only) to obtain intended 2-azido-1,3-diisopropyl-5-methylbenzene (compound 9) as a colorless oil (0.7 g, 75%). $^1$H NMR (400 MHz, $CDCl_3$, 25 °C) δ 6.92 (s, 2H), 3.32 (hept, J=7.1 Hz, 2H), 2.31 (s, 3H), 1.25 (d, J=7.2 Hz, 12H); $^{13}C$ NMR (100 MHz, $CDCl_3$, 25 °C) δ 142.98, 136.42, 124.75, 124.07, 28.88, 23.66, 21.47.

[Example 1] Fluorochrome Release in DMEM Cell Culture Media

Coumarin-ABC (compound 7) and 7-amino-4-methylcoumarin (control compound) which were synthesized in Production Example 3 were each dissolved in water (0.2% DMSO) by 2 μM, and fluorescence spectra were measured. The results are shown in FIG. 1 (dashed line: compound 7, solid line: control compound).

As shown in FIG. 1, it was confirmed that the coumarin-ABC (compound 7) did not emit fluorescence.

Next, the coumarin-ABC (compound 7) (20 μM) in DMEM culture media (Dulbeccos's modified eagle's medium) (100 μL) on a 96-well plate was incubated in the presence or absence of acrolein (20 mM) at room temperature, and fluorescence intensity was measured with use of a spectrofluorometer (SpectraMax iD3, manufactured by Molecular Devices) in a real-time manner for 30 minutes. The results are shown in FIG. 2 (dashed line: in the presence of acrolein, solid line: in the absence of acrolein).

Figure 2:
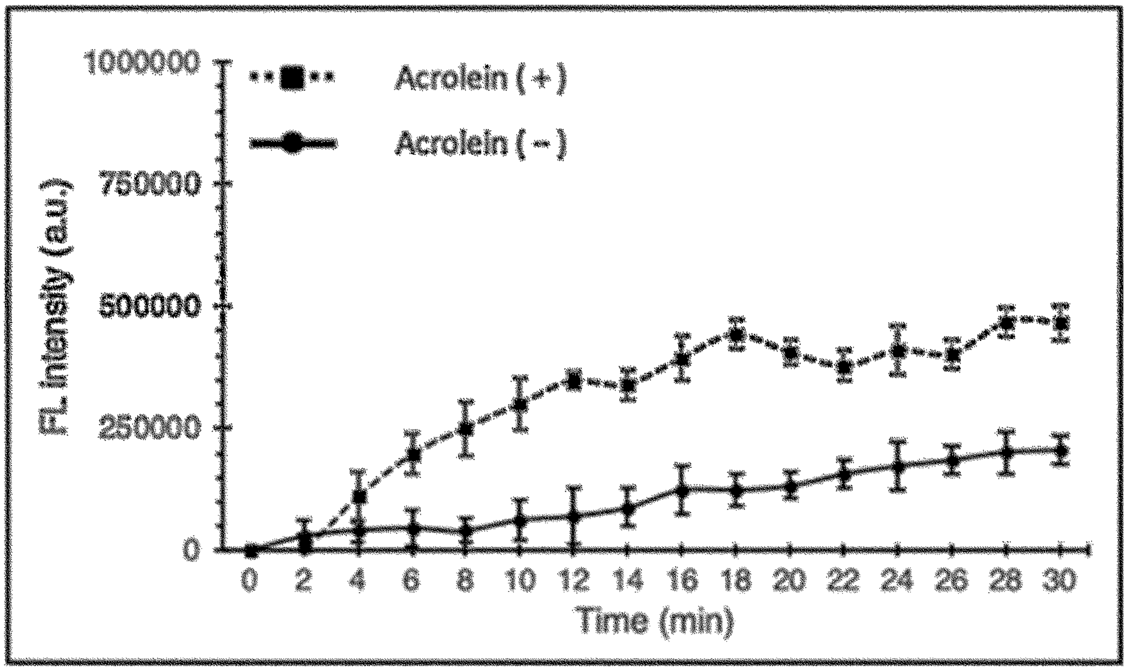
FIG. 2 is a diagram indicating results of measurement in a real-time manner on fluorescence intensity of coumarin-ABC in the presence and absence of acrolein.

As indicated in FIG. 2, a rapid increase in fluorescence intensity was observed in the presence of acrolein. This indicates that the coumarin-ABC (compound 7) reacted with acrolein through azide-acrolein click reaction to release 7-amino-4-methylcoumarin.

[Example 2] Fluorescence Release (Cell-Based Assay; Concentration-Dependent)

Three cell lines [MCF10A (normal human mammary cells), A549 (human lung adenocarcinoma cells), and HeLa S3 (human cervical cancer cells)] were seeded on a 96-well plate ($2\times10^4$ cells/well) and left to attach for 24 hours at 37 °C. Each of the cells was then used for three different conditions as follows:

(Condition 1) The cells were treated with 100 μL of coumarin-ABC (compound 7) solutions [2 μM, 5 μM, 10 μM, 15 μM, 20 μM in the culture medium (1% DMSO)] and incubated for 60 minutes at room temperature.

(Condition 2) The cells were treated with 1 mM of N-acetyl cysteine (NAc-Cys) in the culture medium, and incubated for 2 hours at 37 °C. Next, the cells were treated with 100 μL of coumarin-ABC (compound 7) solutions [2 μM, 5 μM, 10 μM, 15 μM, 20 μM in the culture medium (1% DMSO)] and incubated for 60 minutes at room temperature.

(Condition 3) The cells were treated with 100 μL of 7-amino-4-methylcoumarin solutions [2 μM, 5 μM, 10 μM, 15 μM, 20 μM in the culture medium (1% DMSO)] and incubated for 60 minutes at room temperature.

Figure 4:
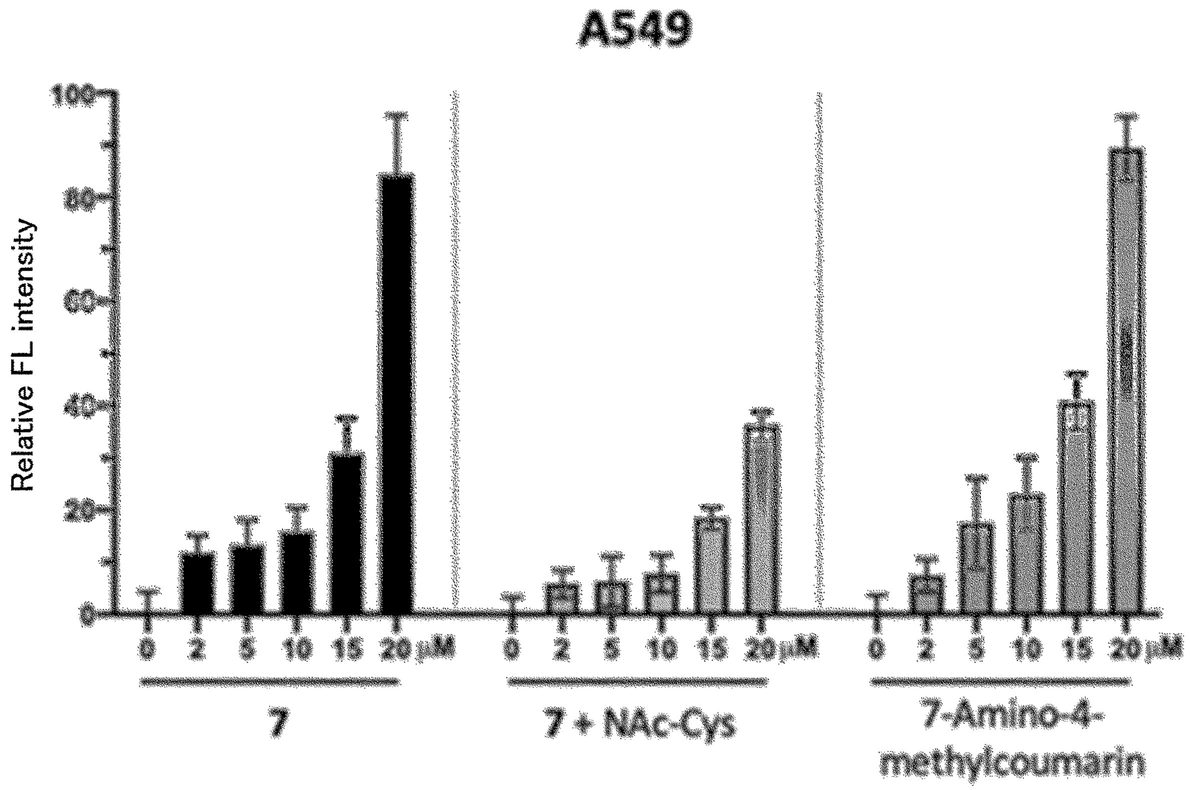
FIG. 4 is a diagram indicating results of measurement of fluorescence intensity of coumarin-ABC and coumarin in A549 (human lung adenocarcinoma cells).
Figure 5:
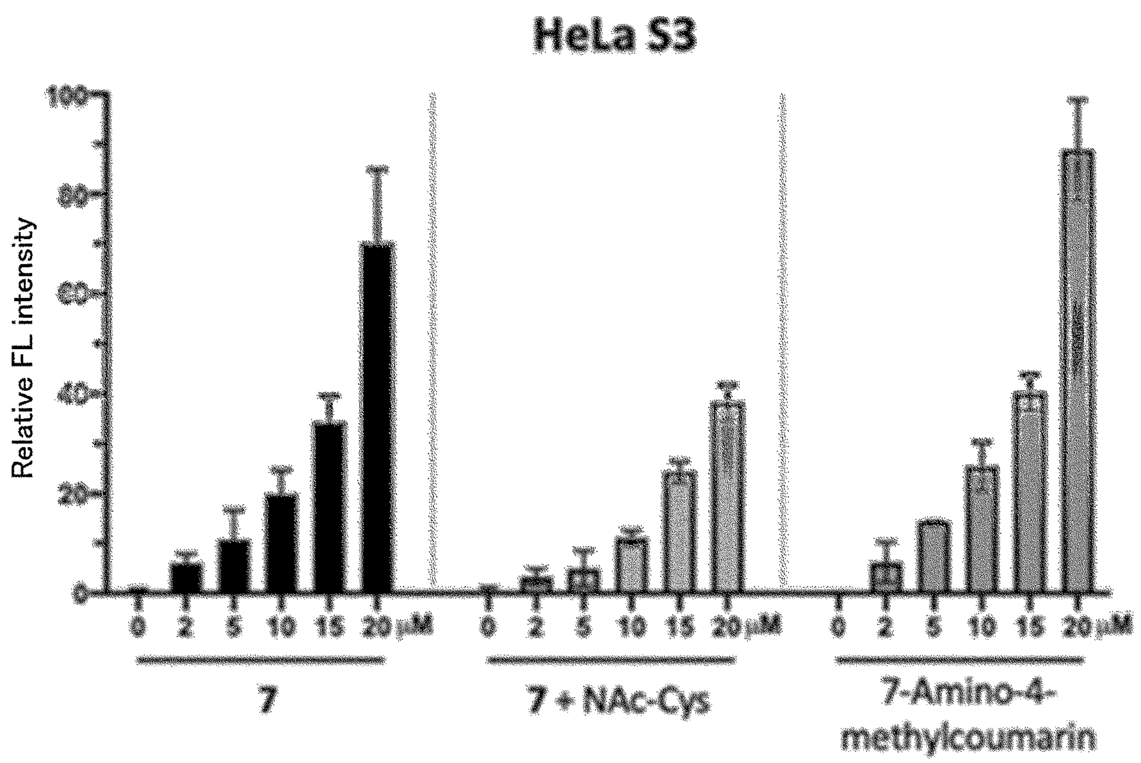
FIG. 5 is a diagram indicating results of measurement (concentration-dependent) of fluorescence intensity of coumarin-ABC and coumarin in HeLa S3 (human cervical cancer cells).

After the incubation, the fluorescence intensity was measured using a spectrofluorometer (SpectraMax iD3, manufactured by Molecular Devices). Fluorescence intensity was normalized for each cell line by the number of 10,000 cells. Results are shown in FIGS. 3 through 5.

Figure 3:
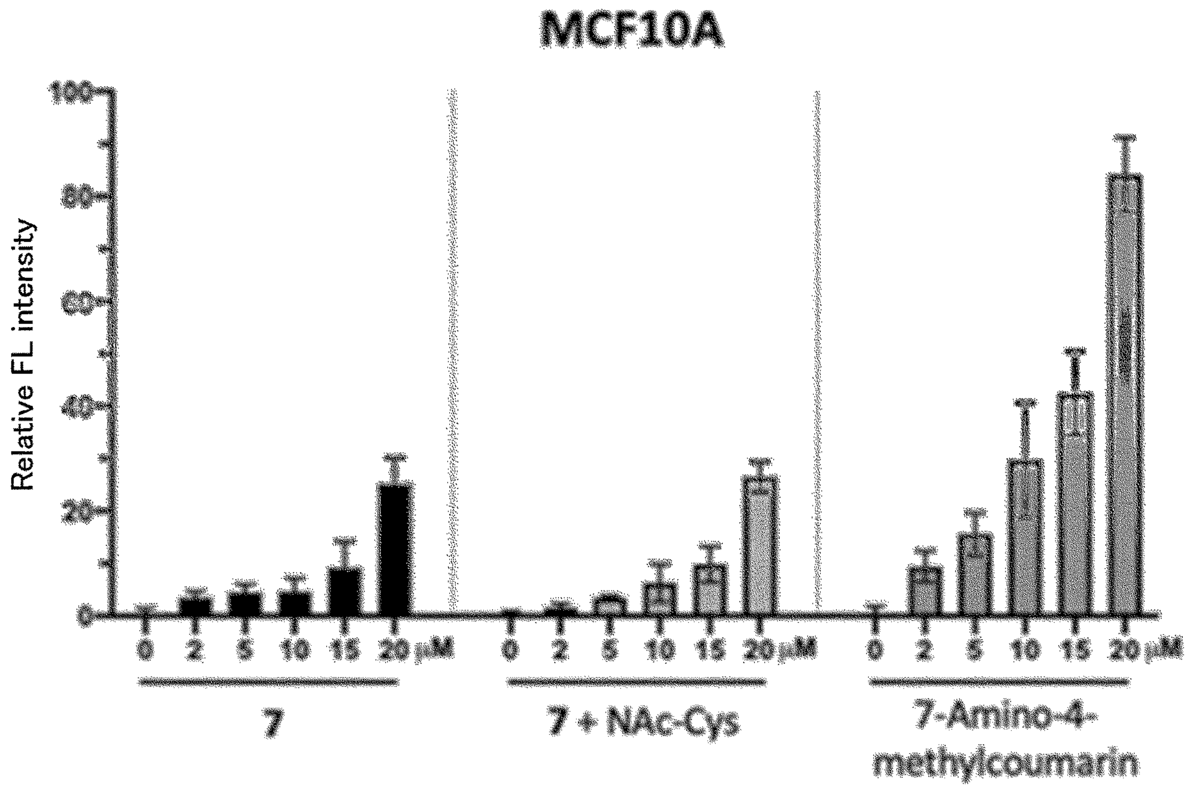
FIG. 3 is a diagram indicating results of measurement of fluorescence intensity of coumarin-ABC and coumarin in MCF10A (normal human mammary cells).

As shown in FIG. 3, for the normal cells incubated under condition 3, release of fluorescence was notably observed depending on the concentration of the compound. Whereas, for the normal cells incubated under condition 1 and condition 2, release of fluorescence was hardly observed. Meanwhile, as shown in FIGS. 4 and 5, for the cancer cells incubated under conditions 1 and 3, release of fluorescence was notably observed depending on the concentration of the compound. Whereas, for the cancer cells incubated under condition 2, release of fluorescence was low. These results indicate that cancer cells overproduce acrolein and therefore, in the cancer cells, the coumarin-ABC (compound 7) reacted with endogenous acrolein through azide-acrolein click reaction to release 7-amino-4-methylcoumarin. Meanwhile, the normal cells produce a very small amount of acrolein, and therefore the most part of the coumarin-ABC (compound 7) was present as it was in the normal cells, and release of fluorescence was low.

[Example 3] Fluorescence Release (Cell-Based Assay; Time-Dependent)

Three cell lines (MCF10A, A549, and HeLa S3) were seeded on a 96-well plate ($2\times10^4$ cells/well) and left to attach for 24 hours at 37 °C. The cells were then treated with 100 μL of coumarin-ABC (compound 7) solutions [2 μM or 20 μM in the culture medium (1% DMSO)] and incubated at room temperature, and fluorescence intensity was measured with use of a spectrofluorometer (SpectraMax iD3, manufactured by Molecular Devices) in a real-time manner for 30 minutes. Fluorescence intensity was normalized for each cell line by the number of 10,000 cells. Results are shown in FIG. 6 (2 μM) and FIG. 7 (20 μM).

Figure 6:
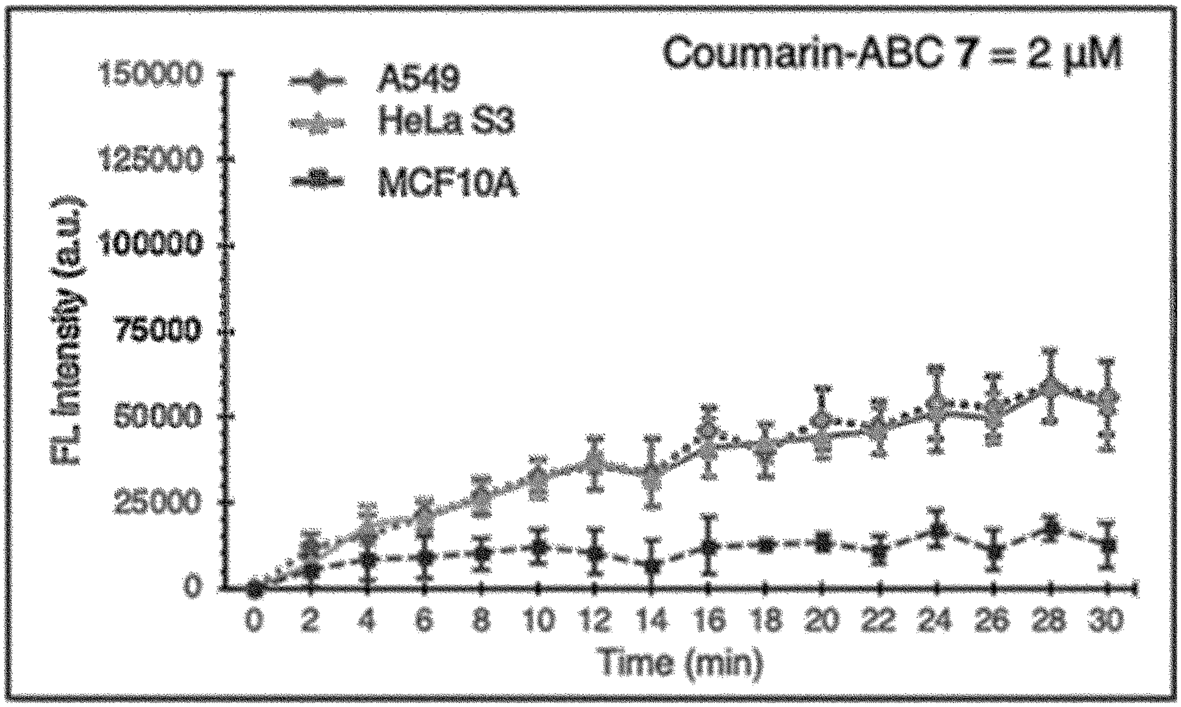
FIG. 6 is a diagram indicating results of measurement in a real-time manner on fluorescence intensity of coumarin-ABC (2 μM) in normal cells and cancer cells.
Figure 7:
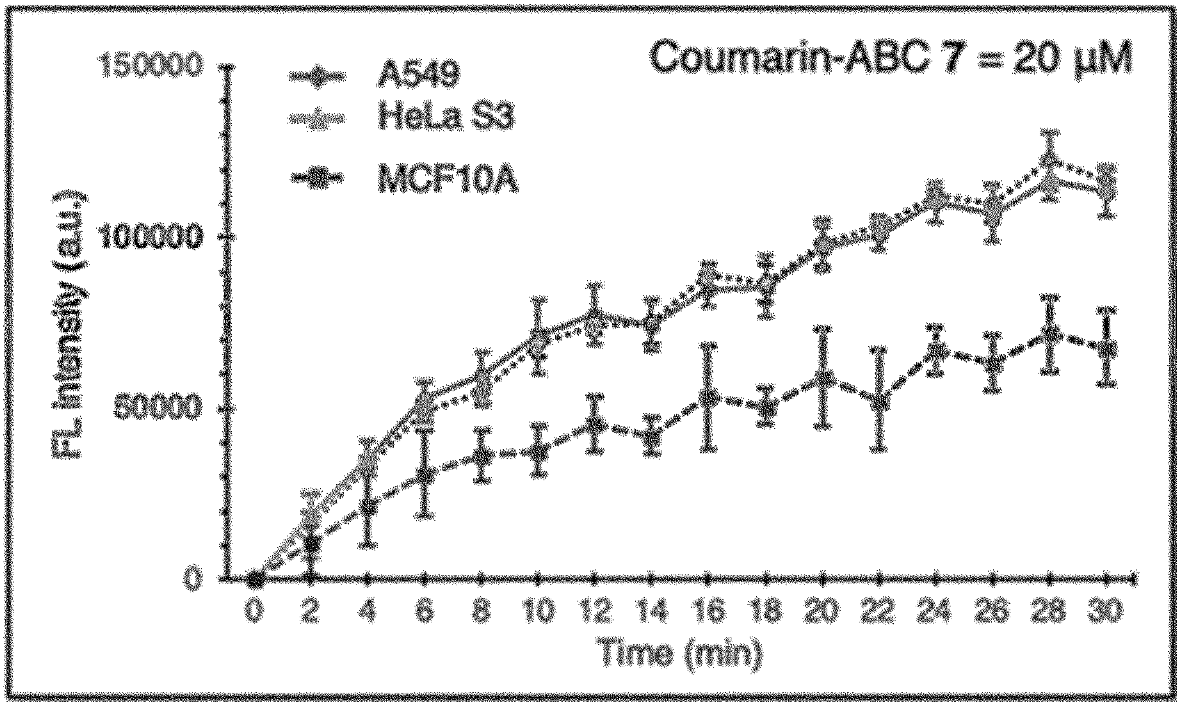
FIG. 7 is a diagram indicating results of measurement in a real-time manner on fluorescence intensity of coumarin-ABC (20 μM) in normal cells and cancer cells.

As shown in FIGS. 6 and 7, release of fluorescence was only slightly observed in the normal cells. In contrast, in the cancer cells, release of fluorescence was notably observed depending on the time. These results indicate that cancer cells overproduce acrolein and therefore, in the cancer cells, the coumarin-ABC (compound 7) reacted with endogenous acrolein through azide-acrolein click reaction to release 7-amino-4-methylcoumarin. Meanwhile, the normal cells produce a very small amount of acrolein, and therefore the most part of the coumarin-ABC (compound 7) was present as it was in the normal cells, and release of fluorescence was low.

[Example 4] Fluorescence Release (HPLC Analysis)

To a solution of coumarin-ABC (compound 7) ($2\times10^{-5}$ mmol, 1.0 eq) in DMSO (1 mL, [compound 7]=20 μM) was added glutathione (GSH) ($2\times10^{-5}$ mmol, 1.0 eq) or acrolein ($2\times10^{-5}$ mmol, 1.0 eq). The reaction liquid was stirred and the reaction mixture was subjected to HPLC analysis at different time intervals (30 minutes, 1 hour, 2 hours, 4 hours, and 12 hours). Conditions of reversed-phase HPLC were as follows: Column, Cosmosil 5C18-AR300 (manufactured by Nacalai Tesque, Inc.) 4.6×250 mm; Mobile phase A, 0.1% TFA in $H_2O$; Mobile phase B, 0.1% TFA in $CH_3CN$; Gradient elution, 0-4 min at 65% B, 4-14 min at 65-95% B, 14-20 min at 95% B; Flow rate at 1 mL/min; Fluorescence detection at 360/450 nm; Amount per injection 6 μL. Results are shown in FIG. 8 (GSH) and FIG. 9 (acrolein).

Figure 8:
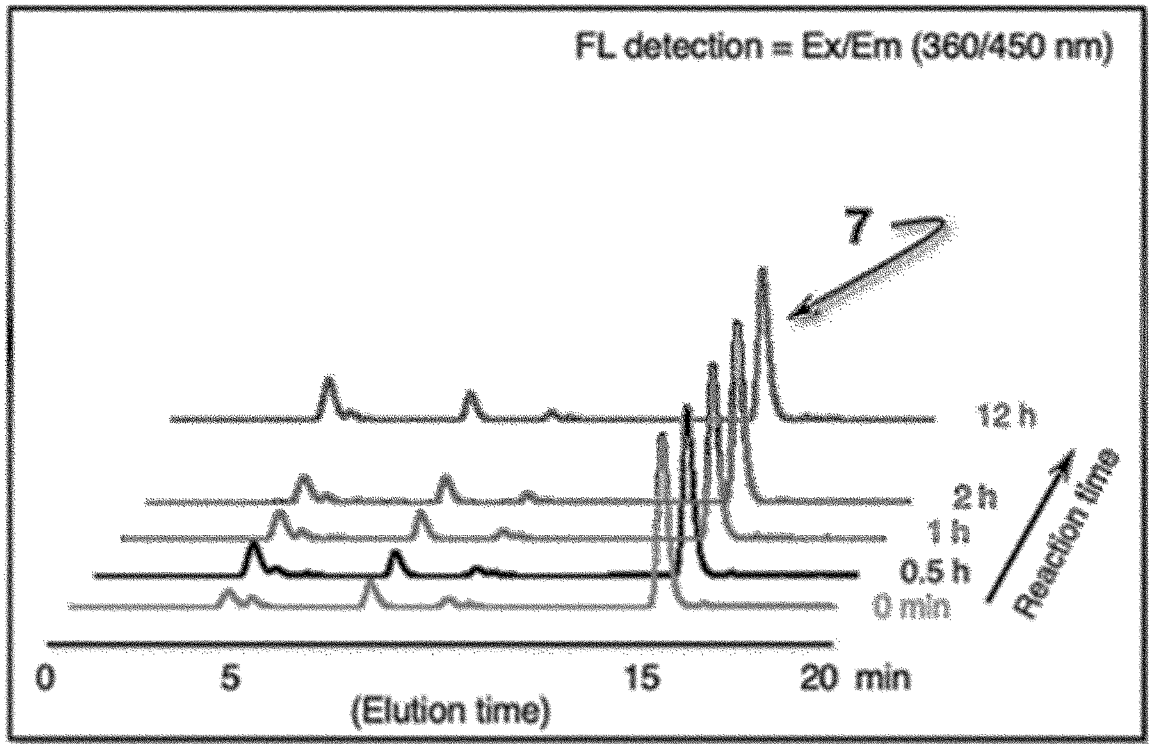
FIG. 8 is a diagram indicating results of HPLC analysis of a mixture of coumarin-ABC and glutathione (GSH).
Figure 9:
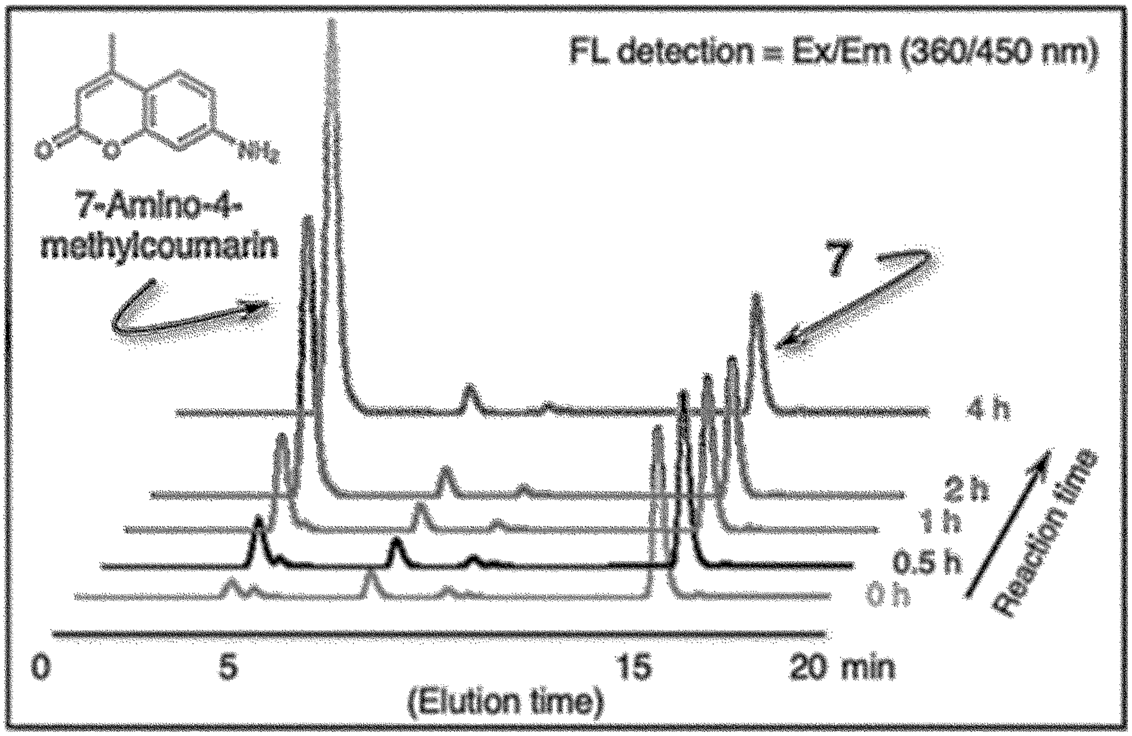
FIG. 9 is a diagram indicating results of HPLC analysis of a mixture of coumarin-ABC and acrolein.

As shown in FIG. 8, the coumarin-ABC (compound 7) and the glutathione (GSH) did not react with each other, and the state of the coumarin-ABC (compound 7) did not change in the mixture which was left for 12 hours. In contrast, as shown in FIG. 9, the coumarin-ABC (compound 7) and acrolein rapidly reacted with each other, and release of 7-amino-4-methylcoumarin was detected in the mixture which was left only for 30 minutes.

[Example 5] ATP Assay (Cytotoxicity Assay)

Three cell lines (MCF10A, A549, and HeLa S3) were seeded on a 96-well plate ($2\times10^4$ cells/well) and left to attach for 24 hours at 37 °C. Each of the cells was then used for three different conditions as follows:

(Condition 1) The cells were treated with 100 μL of MMC-ABC (compound 8) solutions [0.05 μM, 0.1 μM, 0.5 μM, 1 μM, 5 μM, 10 μM, 50 μM in the culture medium (1% DMSO)] and incubated for 48 hours at 37 °C under 5% of $CO_2$.

(Condition 2) Incubation was carried out in a manner similar to that of condition 1 with use of mitomycin C (MMC) solutions.

(Condition 3) The cells were treated with 1 mM of N-acetyl cysteine (NAc-Cys) in the culture medium, and incubated for 2 hours at 37 °C. Then, incubation was carried out in a manner similar to that of condition 1 with use of MMC-ABC (compound 8) solutions.

(Condition 4) Incubation was carried out in a manner similar to that of condition 1 with use of 2-azido-1,3-diisopropyl-5-methylbenzene (compound 9) solutions.

After the incubation, 100 μL of ATP lite 1 step reagent was added to the cells, and the fluorescence intensity was measured using a spectrofluorometer (SpectraMax iD3, manufactured by Molecular Devices). Results are shown in FIG. 10 [MCF10A (normal human mammary cells)] and FIG. 11 [A549 (human lung adenocarcinoma cells) and HeLa S3 (human cervical cancer cells)].

Figure 10:
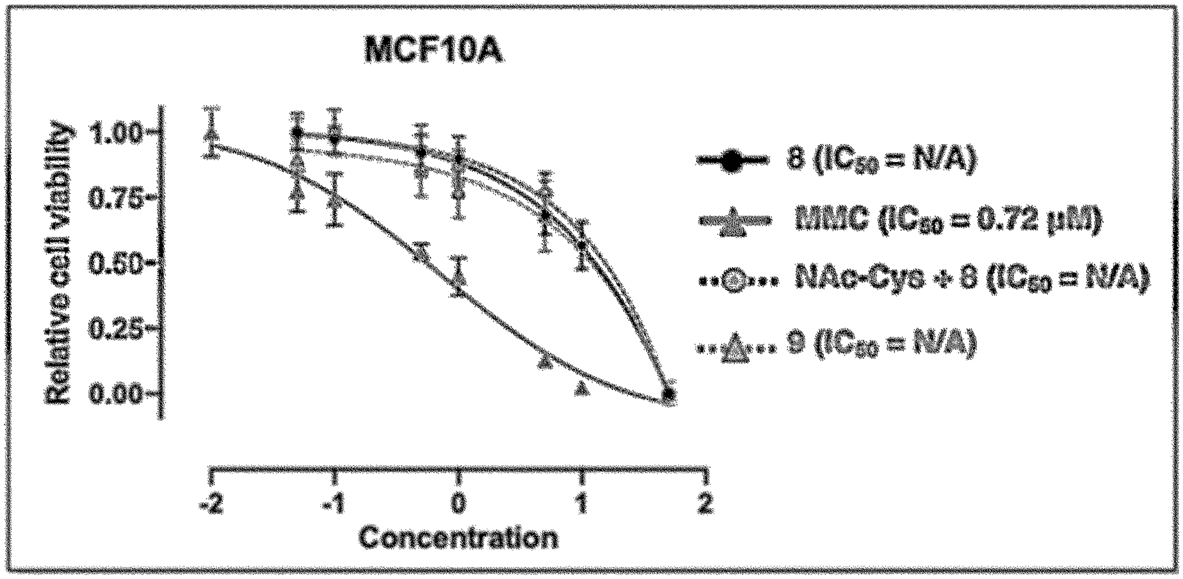
FIG. 10 is a diagram indicating cell viability of MCF10A (normal human mammary cells) in the presence of a complex in accordance with an aspect of the present invention (MMC-ABC) or a control.
Figure 11:
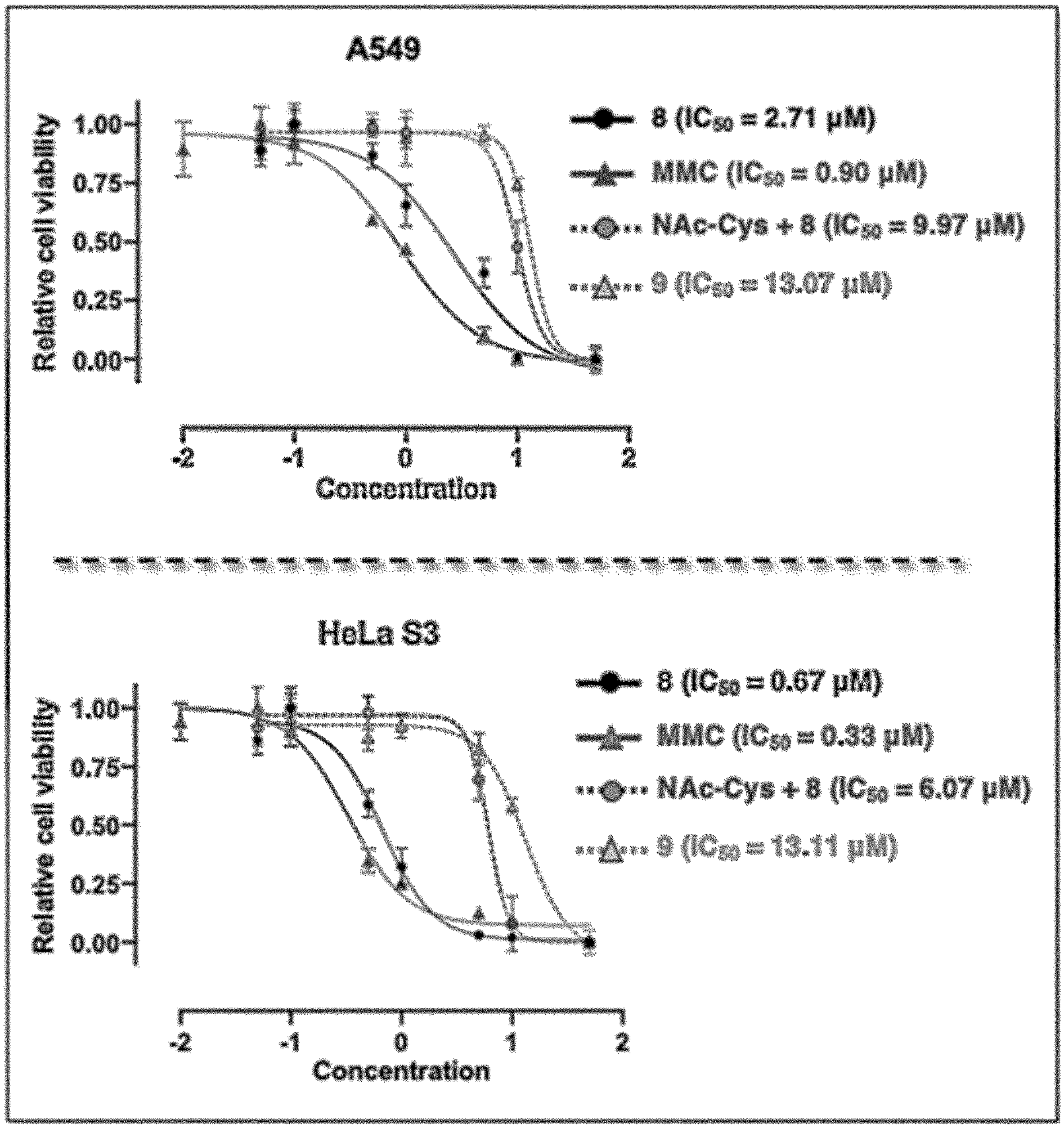
FIG. 11 is a diagram indicating cell viability of A549 (human lung adenocarcinoma cells) and HeLa S3 (human cervical cancer cells) in the presence of MMC-ABC or a control.

As shown in FIGS. 10 and 11, the MMC-ABC (compound 8), which is a prodrug, released free MMC specifically in cancer cells only when reacted with endogenous acrolein which was overproduced by cancer cells. In contrast, MMC nonspecifically exhibited cytotoxicity toward normal cells and cancer cells.

[Example 6] Animal Experiments

The Animal Ethics Committee approved all animal experiments in this Example in advance. For all intratumoral injections and tumor measurements, mice were anesthetized with 2% isoflurane in oxygen at a 2.5-3.0 L/min flow rate.

Cell Lines and Reagents

A549 cells were obtained from stock lines kept in liquid nitrogen. These cells were cultured in Dulbeccos's modified eagle's medium (DMEM) (manufactured by FUJIFILM Wako Pure Chemical Corporation) supplemented with 10% fetal bovine serum (FBS) (manufactured by BioWest) and 1% penicillin-streptomycin (manufactured by Gibco). The cells were then incubated at 37 °C in a 5% $CO_2$ humidified atmosphere.

A549 Tumor Bearing Mice Xenograft Models

A549 xenograft tumors were established in 6-week-old female nude mice BALB/cAJc1-nu/nu by subcutaneous injection of a suspension of 2.5-6.0×$10^6$ cells in 100 μL of cold 50% matrigel in unnourished DMEM into the right and left shoulders, and tumor growth was monitored. The mice were kept in controlled temperature, salinity, and aeration room with sufficient food and water for 12 hours day and 12 hours night. After tumors reached 400-600 $mm^3$ in size, the A549 tumor bearing mice were used for cancer therapy.

Intratumoral (I.T.) Administration

The mice were randomized, divided into five groups, and treated with the prodrugs and controls. Group 1 was intratumorally injected with 10 μL of a vehicle solution (n=10). Group 2 was injected with 10 μL of 1.1 mg/kg of compound 9 (n=10). Group 3 was injected with 10 μL of 1.8 mg/kg of mitomycin C (n=10). Group 4 was injected with 10 μL of 3.1 mg/kg of MMC-ABC (compound 8) (n=6). Group 5 was injected with 10 μL of 2.8 mg/kg of MMC-phenyl azide (compound 10) (n=6).

Note that the MMC-phenyl azide (compound 10) is a control compound which was produced in a manner similar to that of the MMC-ABC (compound 8) synthesized in Production Example 4, except that 4-azido-methanol was used instead of (4-azido-3,5-diisopropylphenyl)-methanol (compound S4) as a starting material.

Figure 12:
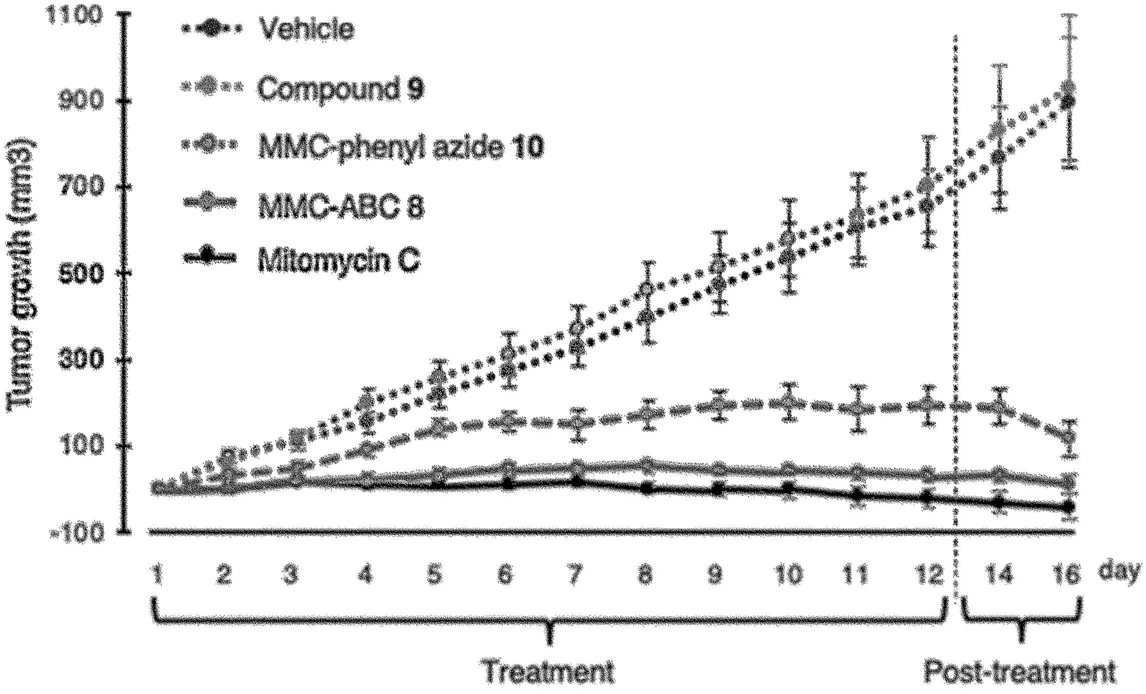
FIG. 12 is a graph indicating change in tumor volume in A549 tumor bearing mice according to intratumoral administration of MMC-ABC or a control.
Figure 13:
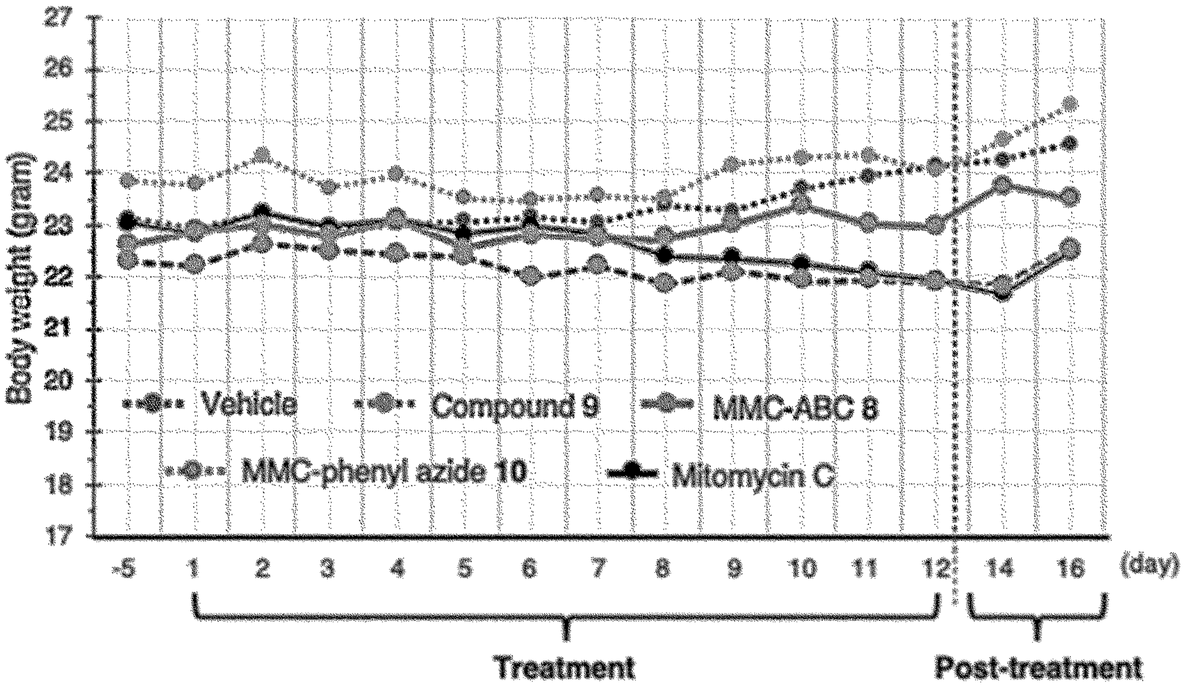
FIG. 13 is a graph indicating change in body weight of A549 tumor bearing mice according to intratumoral administration of MMC-ABC or a control.
Figure 14:
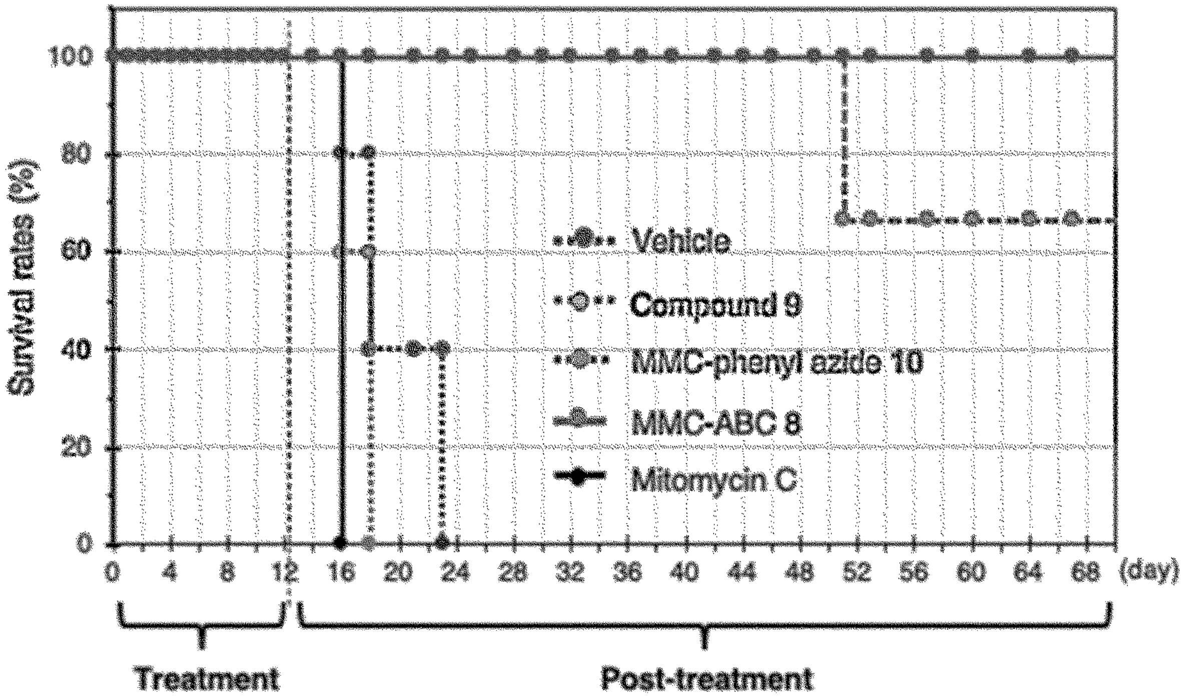
FIG. 14 is a graph indicating survival rates of A549 tumor bearing mice according to intratumoral administration of MMC-ABC or a control.
Figure 15:
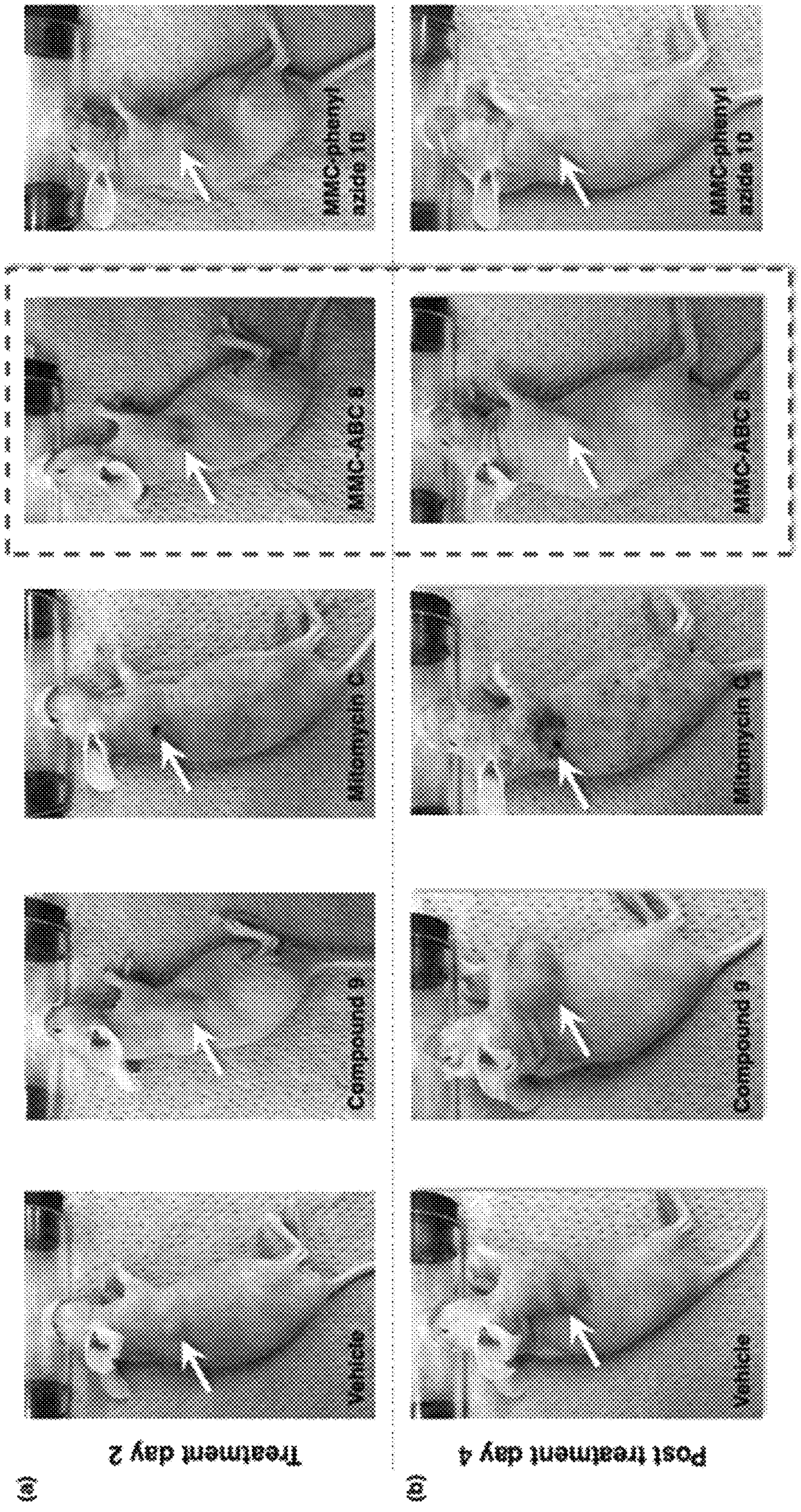
FIG. 15 shows photographs showing states of mice on day 2 of intratumoral administration of MMC-ABC or a control and on day 4 from completion of administration.

The administrations were repeated 12 times in consecutive days with the same doses. The tumor volume and body weight of the mice were recorded every day based on an equation: $V=W^2 \times L/2$, where W and L represented the minor length and major length of the tumor, respectively. When the tumor reached 2,000 $mm^3$, the mice were sacrificed, and the survival rates were calculated using the Kaplan Meier method. Results are shown in FIG. 12 (tumor volume), FIG. 13 (body weight), and FIG. 14 (survival rate). The states of the mice were photographed on day 2 of intratumoral administration and on day 4 from completion of administration. FIG. 15 show the photographs.

As shown in FIGS. 12 through 15, the mice treated with the vehicle or compound 9 had larger tumor sizes. In contrast, it was found that, for the mice treated with mitomycin C and MMC-ABC (compound 8), administration of those was effective with respect to the tumor growth. However, although no side effect was observed in the administration of the prodrug MMC-ABC (compound 8), the mouse treated with the mitomycin C had inflammation on the whole body. In the mouse treated with the MMC-phenyl azide (compound 10), a slight decrease in tumor size was observed as compared with the mice treated with the vehicle or compound 9. However, an inhibitory effect of the MMC-phenyl azide (compound 10) with respect to the tumor growth was smaller, as compared with the MMC-ABC (compound 8).

Intravenous (I.V.) Administration

The mice were randomly assigned to the following groups: Group 1 was intravenously injected with 100 μL of the vehicle solution (n=8). Group 2 was injected with 100 μL of 1.2 mg/kg of compound 9 (n=8). Group 3 was injected with 100 μL of 1.8 mg/kg of mitomycin C (n=9). Group 4 was injected with 100 μL of 3.2 mg/kg of MMC-ABC (compound 8) (n=7). Group 5 was injected with 100 μL of 2.8 mg/kg of MMC-phenyl azide (compound 10) (n=8). Administrations were conducted once in every three days, and 3 times of injections were conducted in total. The tumor volume and body weight of the mice were recorded every day based on an equation: $V=W^2 \times L/2$, where W and L represented the minor length and major length of the tumor, respectively. When the tumor reached 2,000 $mm^3$, the mice were sacrificed, and the survival rates were calculated using the Kaplan Meier method.

The treated mice after the tumor reached 2,000 $mm^3$ were sacrificed and transcardially perfused with 0.9% saline and then followed by 4% paraformaldehyde. The selected organs (liver, kidney, spleen, heart, lung, and tumor) were then taken out, dipped in 4% paraformaldehyde for overnight and followed by 15% and 30% sucrose treatment for overnight each and kept at −80 °C until being used for hematoxylin and eosin (H&E) analysis.

In Vivo Drug Release Study

Groups of A549 tumor bearing mice (in which the tumors had reached 1,000-1,500 $mm^3$) were intratumorally injected with: mitomycin C (3.6 mg/kg, n=2), MMC-ABC (compound 8) (6.2 mg/kg, n=2), and MMC-phenyl azide (compound 10) (5.6 mg/kg, n=2). The mice were sacrificed after 2 hours from the injections of the drugs or prodrugs. The tumors, kidneys, and urines of the treated mice were collected, lysed, and extracted with methanol at 4 °C overnight. The extracts were filtered, evaporated, and partitioned to obtain the crude extracts of the organs, and then analyzed by HPLC.

[Production Example 6] Synthesis of Prodrug PUR-ABC (Compound S6)

In order to synthesize compound S6, first, compound S5 was synthesized along the following route of synthesis.

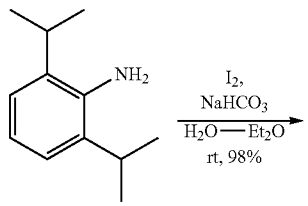

2,6-diisopropylaniline

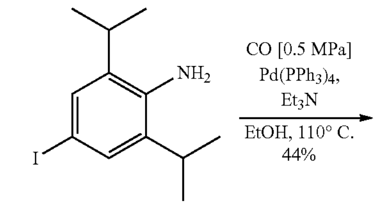

S1

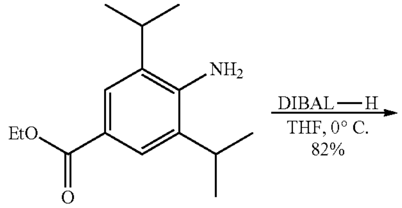

S2

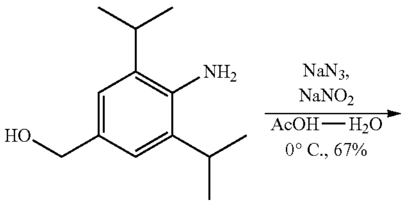

S3

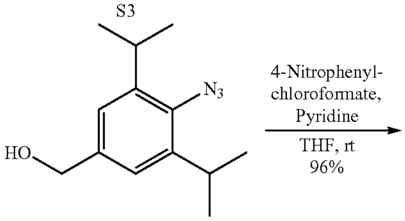

S4

-continued

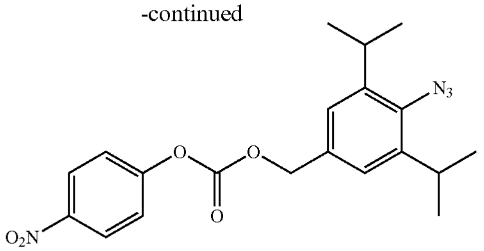

S5

(Production Example 6-1) Synthesis of 4-iodo-2,6-diisopropylaniline (Compound S1)

To a solution of 2,6-diisopropylaniline (2.5 g, 14.1 mmol, 1.0 eq) in a saturated aqueous solution of $NaHCO_3$ and $Et_2O$ (1:1) (140 mL, [2,6-diisopropylaniline]=0.10 M) was added iodine (4.3 g, 16.9 mmol, 1.2 eq). After being stirred for 20 hours at room temperature, $Na_2S_2O_3$ was added, and the mixture was stirred for another 30 minutes. The resulting mixture was extracted with $Et_2O$. The organic layer was washed with saturated saline, dried using $Na_2SO_4$, and filtered. The filtrate was concentrated to dryness under reduced pressure. The residue was purified by silica gel chromatography [n-hexane/EtOAc (9:1 to 7:3)] to obtain intended 4-iodo-2,6-diisopropylaniline (compound S1) as a red-black oil compound (13.5 g, 96%). $^1$H NMR (400 MHz, $CDCl_3$, 25 °C) 67.27 (s, 2H), 3.70 (bs, 2H, $NH_2$), 2.81 (hept, J=6.7 Hz, 2H), 1.21 (d, J=6.8 Hz, 12H); $^{13}$C NMR (100 MHz, $CDCl_3$, 25 °C) 6140.27, 135.08, 131.79, 81.12, 27.82, 22.21; ESI-HRMS m/z calculated for $C_{12}H_{19}IN$ ($[M+H]^+$) 304.0557, found 304.0558.

(Production Example 6-2) Synthesis of Ethyl 4-amino-3,5-diisopropylbenzoate (Compound S2)

To a solution of 4-iodo-2,6-diisopropylaniline which is compound S1 (1.4 g, 4.7 mmol, 1.0 eq) and $Pd(PPh_3)_4$ (0.11 g, 0.094 mmol, 0.02 eq) in EtOH (30 mL, [S1]=0.16 M) was added $Et_3N$ (1.6 mL, 12 mmol, 2.5 eq). The resulting solution was stirred under CO pressure (0.5 Mpa) at 110 °C for 28 hours. The resulting suspension was filtered through Celite, and the filtrate was concentrated to dryness under reduced pressure. The residue was purified by silica gel column chromatography [n-hexane/EtOAc (hexane only to 9:1)] to obtain intended ethyl 4-amino-3,5-diisopropylbenzoate (compound S2) as a yellow oil compound (0.51 g, 44%). $^1$H MMR (400 MHz, $CDCl_3$, 25 °C) δ 7.75 (s, 2H), 4.34 (q, J=7.1 Hz, 2H), 4.16 (bs, 2H, $NH_2$), 2.88 (hept, J=6.9 Hz, 2H), 1.38 (t, J=7.2 Hz, 3H), 1.29 (d, J=6.8 Hz, 12H); $^{13}$C NMR (100 MHz, $CDCl_3$, 25 °C) 6167.64, 145.10, 131.37, 125.04, 119.77, 60.30, 27.97, 22.24, 14.55; ESI-HRMS m/z calculated for $C_{15}H_{24}NO_2$ ($[M+H]^+$) 250.1802, found 250.1805.

(Production Example 6-3) Synthesis of 4-hydroxymethyl-2,6-diisopropylaniline (compound S3)

A solution of compound S2 (513 mg, 2.1 mmol, 1.0 eq) in THE (30 mL, [S2]=1.0 M) was cooled down to 0 °C, and then DIBAL-H (6.2 mL of a 1 M solution in toluene, 6.2 mmol, 3.0 eq) was added by dripping. The reaction temperature was raised to room temperature, and stirring was carried out for 30 minutes. The reaction temperature was decreased to 0 °C, and excessive DIBAL-H was quenched with MeOH. The resulting mixture was filtered through Celite while being washed with MeOH, and the filtrate was concentrated to dryness under reduced pressure. The residue was purified by silica gel column chromatography [n-hexane/EtOAc (9:1 to 7:3)] to obtain intended 4-hydroxymethyl-2,6-diisopropylaniline (compound S3) as an orange oil compound (346 mg, 82%). $^1$H NMR (400 MHz, $CDCl_3$, 25 °C) 67.04 (s, 2H), 4.55 (s, 2H), 3.74 (bs, 2H, $NH_2$), 2.92 (hept, J=6.7 Hz, 2H), 1.27 (d, J=6.8 Hz, 12H); $^{13}$C NMR (100 MHz, $CDCl_3$, 25 °C) δ 140.06, 132.71, 130.89, 122.46, 66.09, 27.99, 22.44; ESI-HRMS m/z calculated for $C_{13}H_{22}NO$ ($[M+H]^+$) 208.1696, found 208.1699.

(Production Example 6-4) Synthesis of (4-azido-3, 5-diisopropylphenyl)-methanol (Compound S4)

A solution of compound S3 (346 mg, 1.7 mmol, 1.0 eq) in acetic acid and distilled water (2:1) (18 mL, [S3]=0.94 M) was cooled down to 0 °C, and then $NaN_3$ (461 mg, 7.1 mmol, 4.2 eq) was added, and immediately $NaNO_2$ (477 mg, 6.9 mmol, 4.1 eq) was added. After stirring for 2 hours at 0 °C, a saturated aqueous solution of $NaHCO_3$ was added until the solution became pH 7. The mixture was extracted with EtOAc. The organic layer was washed with saturated saline, dried with $Na_2SO_4$, and then filtered. The filtrate was concentrated to dryness under reduced pressure. The residue was purified by silica gel column chromatography [n-hexane/EtOAc (9:1 to 7:3)] to obtain intended (4-azido-3,5-diisopropylphenyl)-methanol (compound S4) as a yellow oil compound (260 mg, 67%). $^1$H NMR (400 MHz, $CDCl_3$, 25 °C) 67.13 (s, 2H), 4.64 (s, 2H), 3.36 (p, J=6.8 Hz, 2H), 1.27 (d J=6.7 Hz, 12H); $^{13}$C NMR (100 MHz, $CDCl_3$, 25 °C) 6143.51, 139.31, 134.84, 122.79, 65.27, 28.90, 23.52; ESI-HRMS m/z calculated for $C_{13}H_{20}N_3O$ ($[M+H]^+$) 234.1601, found 234.1605.

(Production Example 6-5) Synthesis of 4-azido-3,5-diisopropylbenzyl-(4-nitrophenyl)-carbonate (Compound S5)

To a solution of compound S4 (260 mg, 1.1 mmol, 1.0 eq) and 4-nitrophenyl chloroformate (270 mg, 1.3 mmol, 1.2 eq) in THF (12 mL, [S4]=0.09 M) was added pyridine (181 μL, 2.2 mmol, 2 eq). The reaction mixture was stirred under argon atmosphere at room temperature for 2 hours. The THF solvent was removed with use of a rotary evaporator, and the residue was partitioned with EtOAc-$H_2O$. The organic layer was washed with saturated saline, then dried with $Na_2SO_4$, and filtered. The filtrate was evaporated to dryness under reduced pressure. The residue was purified by silica gel column chromatography [n-hexane/EtOAc (n-hexane only to 20:1)] to obtain intended 4-azido-3,5-diisopropylbenzyl-(4-nitrophenyl)-carbonate (compound S5) (426 mg, 96%). $^1$H NMR (400 MHz, $CDCl_3$, 25 °C) 68.27 (d, J=9.1 Hz, 2H), 7.20 (s, 2H), 5.26 (s, 2H), 3.38 (p, J=6.9 Hz), 1.29 (d, J=6.9, 12H); $^{13}$C NMR (100 MHz, $CDCl_3$, 25 °C) 6155.65, 152.50, 145.52, 143.82, 136.11, 132.62, 125.41, 124.63, 121.86, 71.07, 28.94, 23.53.

[Production Example 6-6] Synthesis of Prodrug PUR-ABC (Compound S6)

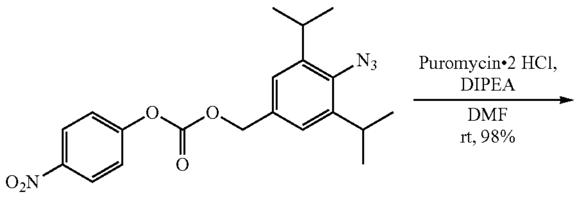

S5

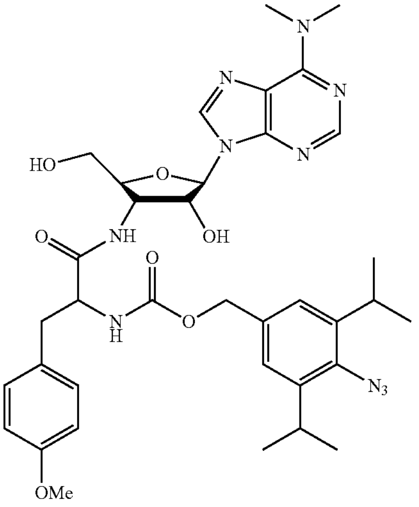

S6

To a solution of compound S5 (13 mg, 0.033 mmol, 1.0 eq) in DMF (500 μL, [S5]=0.07 M) was added DIPEA (52 μL, 0.33 mmol, 10 eq), and the mixture was well stirred, and then puromycin dihydrochloride (27 mg, 0.05 mmol, 1.5 eq) was added. The reaction mixture was stirred at room temperature for 18 hours. Toluene was added to the reaction mixture, and a volatile substance was removed by a rotary evaporator. The residue was purified by silica gel column chromatography [$CHCl_3$/MeOH (50:1 to 20:1)] to obtain intended PUR-ABC (compound S6) as a yellow oil compound (24 mg, 98%). $^1$H NMR (400 MHz, $CDCl_3$) δ 8.02 (s, 1H), 7.89 (s, 1H), 7.14 (d, J=8.1 Hz, 2H), 7.08 (s, 2H), 6.86 (d, J=8.6 Hz, 2H), 6.50 (d, J=5.0 Hz, 1H), 5.59 (d, J=7.8 Hz, 2H), 5.42 (d, J=5.0 Hz, 1H), 5.07 (d, J=12.0 Hz, 1H), 4.98 (d, J=11.9 Hz, 1H), 4.76 (t, J=5.7 Hz, 1H), 4.43 (d, J=6.8 Hz, 1H), 4.36 (q, J=5.8 Hz, 1H), 4.04 (dt, J=4.3, 2.0 Hz, 1H), 3.88 (d, J=12.6 Hz, 1H), 3.75 (s, 3H), 3.33 (hept, J=6.6 Hz, 4H), 3.11 (dd, J=13.9, 6.3 Hz, 1H), 3.02-2.82 (m, 2H), 2.14-1.99 (m, 3H), 1.69 (s, 1H), 1.24 (d, J=6.9 Hz, 12H), 0.87 (s, 1H). $^{13}$C NMR (101 MHz, $CDCl_3$) δ 172.17, 159.02, 155.09, 151.71, 148.84, 143.73, 137.80, 135.60, 134.54, 130.55, 128.55, 124.22, 121.34, 114.60, 91.17, 85.18, 72.99, 67.51, 62.70, 56.92, 55.60, 51.99, 38.65, 29.11, 28.52, 26.23, 23.72. ESI-MS m/z calculated for $C_{36}H_{47}N_{10}O_7$ ($[M+H]^+$) 731.3624, found 731.3938.

[Production Example 7] Synthesis of Prodrug DOX-ABC (Compound S7)

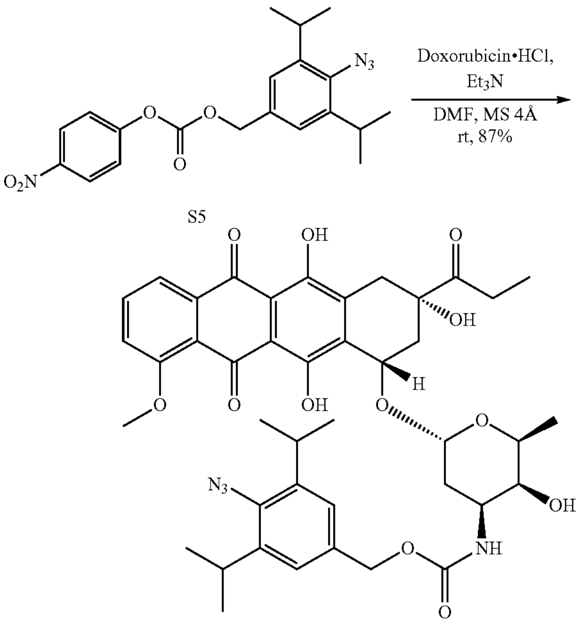

S5

S7

To a solution of compound S5 (80.2 mg, 0.20 mmol, 1.0 eq), doxorubicin hydrochloride (105 mg, 0.17 mmol, 0.9 eq), and molecular sieves (MS 4A) in DMF (2 mL, [S5]=0.1 M) was added $Et_3N$ (57 μL, 0.40 mmol, 2.0 eq). The reaction mixture was stirred under nitrogen atmosphere for 20 hours. The resulting mixture was filtered through Celite while being washed with EtOAc, and the filtrate was concentrated to dryness under reduced pressure. The residue was partitioned with EtOAc-$H_2O$. The organic layer was washed with saturated saline, dried with $Na_2SO_4$, and filtered. The filtrate was concentrated to dryness under reduced pressure. The residue was purified by silica gel column chromatography $CHCl_3$/MeOH (25:1) to obtain intended DOX-ABC (compound S7) as a red solid (120 mg, 87%). $^1H$ NMR (400 MHz, $CDCl_3$, 25 °C) δ7.95 (d, J=7.7 Hz, 1H), 7.74 (t, J=8.0 Hz, 1H), 7.36 (d, J=8.7 Hz, 1H), 7.05 (s, 2H), 5.49 (bs, 1H, NH), 5.34-5.18 (m, 2H), 4.97 (s, 2H), 4.76 (d, J=4.6 Hz, 2H), 4.54 (s, 1H), 4.14 (dd, J=14.7, 7.2 Hz, 1H), 4.05 (s, 3H), 3.93-3.82 (m, 1H), 3.68 (d, J=7.8 Hz, 1H), 3.30 (p, J=6.9 Hz, 2H), 3.18 (d, J=18.5 Hz, 1H), 3.12 (t, J=6.0 Hz, 1H), 2.85 (d, J=18.8 Hz, 1H), 2.33 (d, J=14.6 Hz, 2H), 2.15 (dd, J=14.8, 4.1 Hz, 1H), 1.84 (ddd, J=27.1, 13.1, 4.5 Hz, 2H), 1.30 (d, J=6.5 Hz, 3H), 1.22 (d, J=6.9 Hz, 12H); $^{13}C$ NMR (100 MHz, $CDCl_3$, 25 °C) δ213.96, 186.91, 186.51, 161.05, 156.22, 155.62, 155.55, 143.42, 135.84, 135.38, 135.25, 134.70, 133.64, 124.01, 120.71, 119.88, 118.57, 111.52, 111.52, 111.36, 100.86, 76.66, 69.81, 69.67, 67.41, 66.85, 65.62, 56.69, 47.15, 35.67, 33.95, 30.26, 28.88, 23.49, 16.92; ESI-HRMS m/z calculated for $C_{41}H_{46}N_4NaO_{13}$ ($[M+H]^+$) 825.2954, found 825.2954.

[Example 7] ATP Assay (Cytotoxicity Assay)

Three cell lines (MCF10A, A549, and HeLa S3) were seeded on a 96-well plate ($2\times10^4$ cells/well) and left to attach for 24 hours at 37 °C. Each of the cells was then used for two different conditions as follows:

(Condition 1) The cells were treated with 100 μL of DOX-ABC (compound 7) solutions [0.05 μM, 0.1 μM, 0.5 μM, 1 μM, 5 μM, 10 μM, 50 μM in the culture medium (1% DMSO)] and incubated for 48 hours at 37 °C under 5% of $CO_2$.

(Condition 2) Incubation was carried out in a manner similar to that of condition 1 with use of doxorubicin (DOX) solutions.

After the incubation, 100 μL of ATP lite 1 step reagent was added to the cells, and the fluorescence intensity was measured using a spectrofluorometer (SpectraMax iD3, manufactured by Molecular Devices). Results are shown in FIG. 16.

Figure 16:
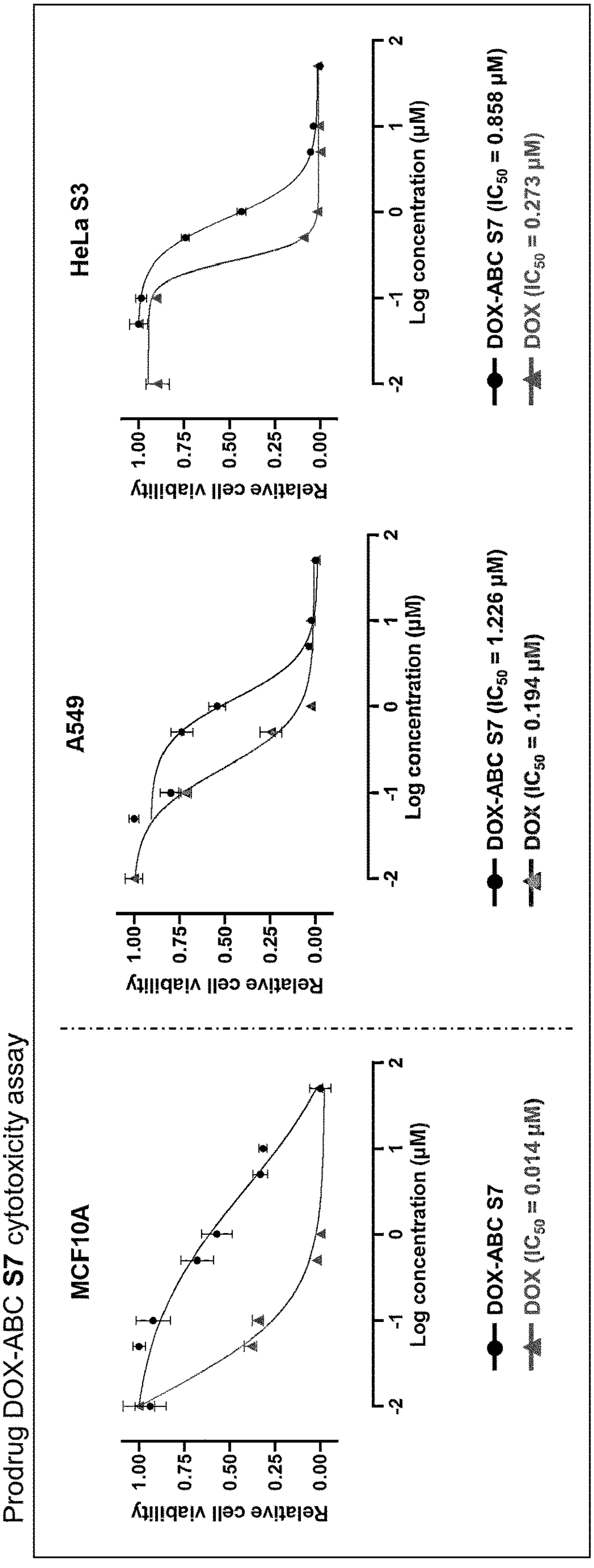
FIG. 16 is a diagram indicating cell viability of MCF10A, A549, and HeLa S3 in the presence of DOX-ABC and DOX.

As shown in FIG. 16, the DOX-ABC (compound 7), which is a prodrug, released free DOX specifically in cancer cells only when reacted with endogenous acrolein which was overproduced by cancer cells. In contrast, DOX non-specifically exhibited cytotoxicity toward normal cells and cancer cells.

[Example 8] Animal Experiments

A549 tumor bearing mice xenograft models were prepared in a manner similar to that in Example 6. The prepared mice were randomized, divided into three groups, and treated with the prodrugs and controls. Group 1 was intratumorally injected with 10 μL of compound 9 produced in Production Example 5 as a control (n=10). Group 2 was intratumorally injected with 10 μL of doxorubicin (n=10). Group 3 was intratumorally injected with 10 μL of compound S7 (n=10).

Administrations were conducted 4 times in total on days 0, 4, 7, and 11 with the same doses. The tumor volumes of the mice were recorded every day based on an equation: $V=W^2\times L/2$, where W and L represented the minor length and major length of the tumor, respectively. When the tumor reached 2,000 $mm^3$, the mice were sacrificed, and the survival rates were calculated using the Kaplan Meier method.

Figure 17:
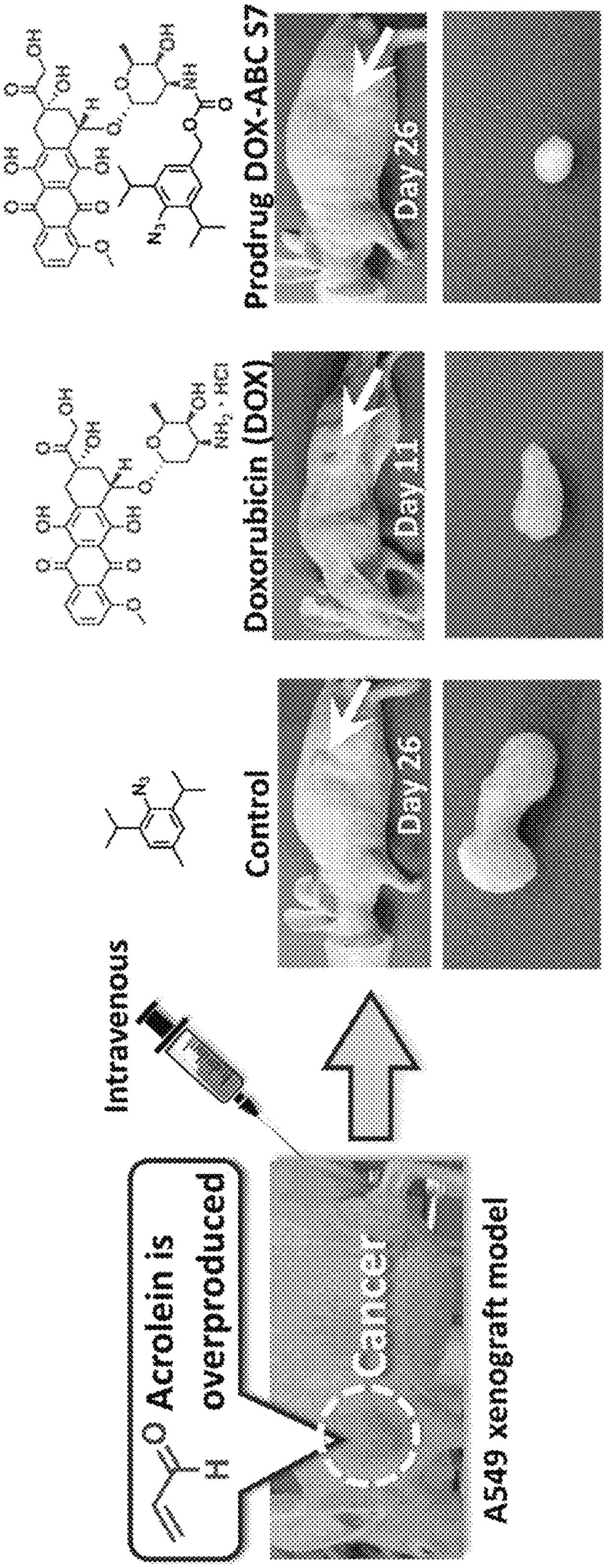
FIG. 17 shows photographs showing states of mice after intratumoral administration of a control (compound 9), DOX, or DOX-ABC.

FIG. 17 shows photographs of the mouse on day 26 of intratumoral administration in group 1 (control, compound 9), the mouse on day 11 of intratumoral administration in group 2 (doxorubicin), and the mouse on day 26 of intratumoral administration in group 3 (compound S7).

Figure 18:
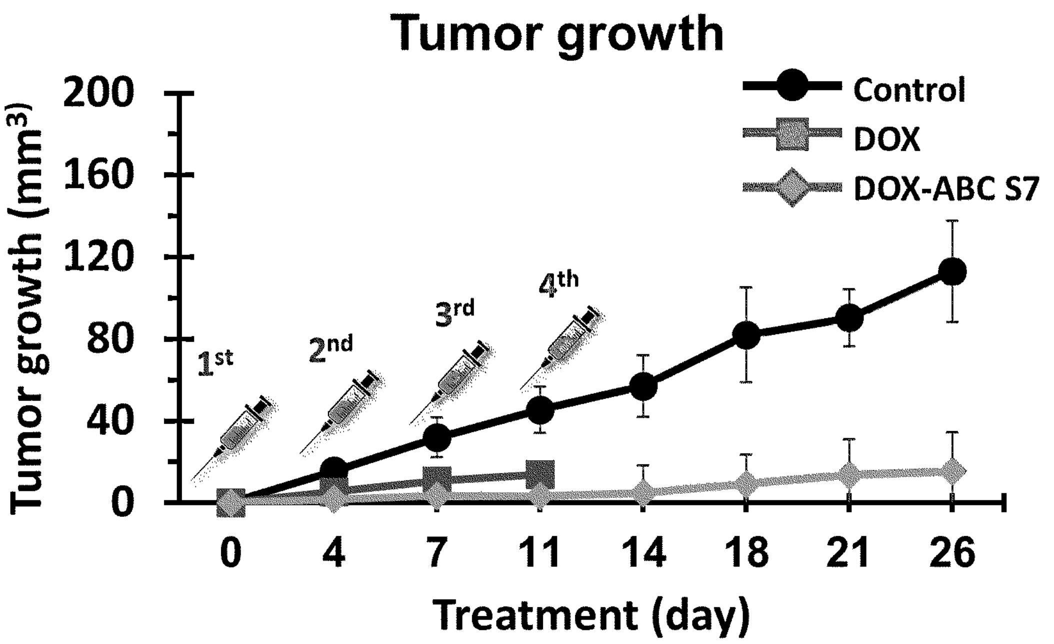
FIG. 18 is a graph indicating change in tumor volume in A549 tumor bearing mice according to intratumoral administration of a control (compound 9), DOX, or DOX-ABC.
Figure 19:
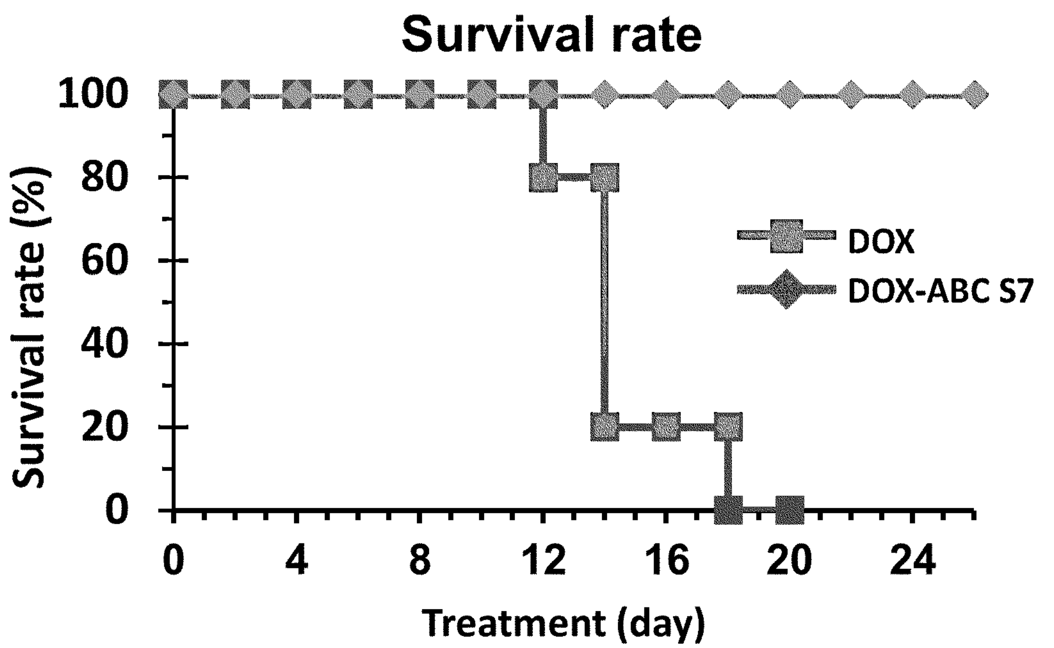
FIG. 19 is a graph indicating survival rates of A549 tumor bearing mice according to intratumoral administration of a control (compound 9), DOX, or DOX-ABC.

FIG. 18 shows a graph indicating change in tumor volume. FIG. 19 shows a graph indicating change in survival rate. The horizontal axis in FIGS. 18 and 19 represents the number of days elapsed from the start of intratumoral administration.

As shown in FIGS. 17 through 19, the mice treated with compound 9 had a larger tumor size. In contrast, it was found that, for the mice treated with doxorubicin and DOX-ABC (compound S7), administration of those was effective with respect to the tumor growth. However, the survival rate of the mouse treated with doxorubicin suddenly decreased at and after the fourth intratumoral administration. The survival rate of the mouse treated with DOX-ABC (compound S7) was 100% even at and after the fourth intratumoral administration.

[Example 9] Animal Experiments

A549 tumor bearing mice xenograft models were prepared in a manner similar to that in Example 6. The prepared mice were randomized, divided into two groups, and treated with the prodrugs and controls. Group 1 was intratumorally injected with 10 µL of compound 9 as a control (n=10). Group 2 was intratumorally injected with 10 µL of compound S6 (n=10).

Administrations were conducted 4 times in total on days 0, 4, 7, and 11 with the same doses. The tumor volumes of the mice were recorded every day based on an equation: $V=W^2 \times L/2$, where W and L represented the minor length and major length of the tumor, respectively.

Figure 20:
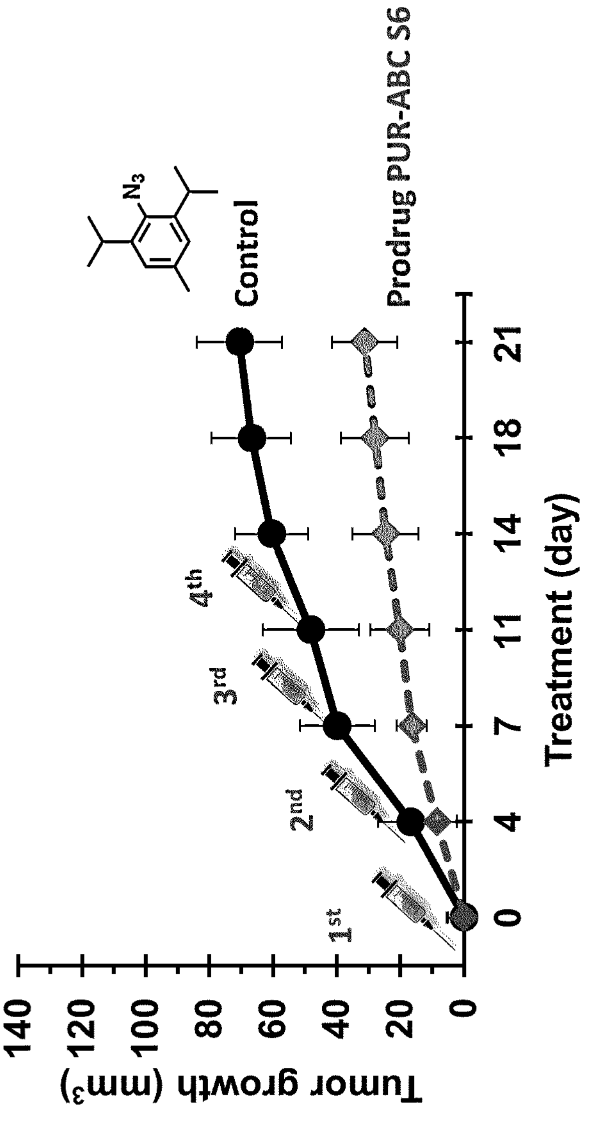
FIG. 20 is a graph indicating change in tumor volume in A549 tumor bearing mice according to intratumoral administration of a control (compound 9) or PUR-ABC.
Figure 20:
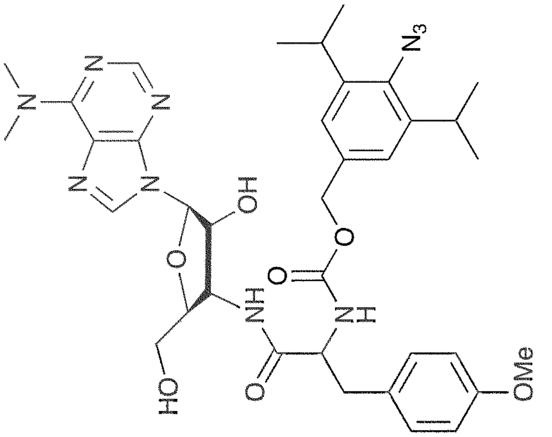

FIG. 20 shows a graph indicating change in tumor volume. The horizontal axis in FIG. 20 represents the number of days elapsed from the start of intratumoral administration.

As shown in FIG. 20, it was found that, for the mice treated with PUR-ABC (compound S6), the administration was effective with respect to the tumor growth.

INDUSTRIAL APPLICABILITY

The present invention can be used as a therapeutic agent for a tumor and a diagnostic drug for determining the presence or absence of a tumor, and can be used for, for example, life science research and medical treatment.

The invention claimed is:

1. A complex comprising:

an acrolein-reactive site having a chemical structure represented by Formula (1); and a leaving site having another chemical structure, the leaving site binding to the acrolein-reactive site via a linker that is cleavable by a reaction between the acrolein-reactive site and acrolein, (1)

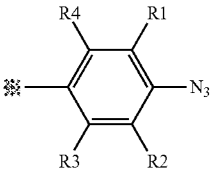

wherein

R1 and R2 each independently represent a hydrogen atom, a halogen atom, or an alkyl group that has 1 to 5 carbon atoms and that may be substituted by at least one halogen atom, provided that at least one of R1 and R2 is the alkyl group having 1 to 5 carbon atoms;

R3 and R4 each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms (provided that a hydrogen atom constituting the alkyl group may be substituted by a substituent selected from a halogen atom, a hydroxy group, and an amino group that may have a substituent); and ※ is a binding site to the linker, wherein the linker is a linker having a chemical structure represented by Formula (2):

(2)

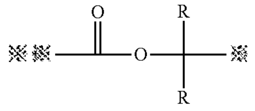

wherein two R each independently represent a hydrogen atom, a halogen atom, a hydroxy group, a thiol group, an amino group that may have a substituent, an alkoxy group having 1 to 5 carbon atoms, an alkylthio group having 1 to 5 carbon atoms, or an alkyl group having 1 to 5 carbon atoms (provided that a hydrogen atom constituting the alkyl group may be substituted by a substituent selected from a halogen atom, a hydroxy group, and an amino group that may have a substituent);

※ is a binding site to the acrolein-reactive site; and

※※ is a binding site to the leaving site, wherein R1 and R2 in Formula (1) each independently represent an alkyl group that has 1 to 5 carbon atoms and that may be substituted by at least one halogen atom, and wherein the leaving site is an antitumor compound or a labelled compound.

2. The complex as set forth in claim 1, wherein:

※※ in Formula (2) is a binding site to a nitrogen atom, a sulfur atom, or an oxygen atom contained in the leaving site.

3. The complex as set forth in claim 2, wherein:

two R in Formula (2) each independently represent a hydrogen atom, a halogen atom, or an alkyl group having 1 to 5 carbon atoms (provided that a hydrogen atom constituting the alkyl group may have a substituent selected from a halogen atom, a hydroxy group, and an amino group that may have a substituent).

4. The complex as set forth in claim 1, wherein:

the leaving site is the antitumor compound.

5. The complex as set forth in claim 1, wherein:

the leaving site leaves by reacting with acrolein that is present around a tumor cell.

6. A therapeutic agent for a tumor, said therapeutic agent comprising the complex recited in claim 4.

7. A method for causing a leaving site to leave, said method comprising the step of:

causing the complex recited in claim 1 to react with acrolein.

8. A therapeutic agent for a tumor, said therapeutic agent comprising the complex recited in claim 5.

9. A method for causing a leaving site to leave, said method comprising the step of:

causing the therapeutic agent recited in claim 8 to react with acrolein.

* * * * *